United States Patent [19]

Franke

[11] Patent Number: 5,955,297
[45] Date of Patent: *Sep. 21, 1999

[54] EXPRESSION PLASMIDS FOR IMPROVED PRODUCTION OF HETEROLOGOUS PROTEIN IN BACTERIA

[75] Inventor: Arthur E. Franke, Groton, Conn.

[73] Assignee: Pfizer Inc., New York, N.Y.

[*] Notice: This patent is subject to a terminal disclaimer.

[21] Appl. No.: 07/892,598

[22] Filed: May 29, 1992

Related U.S. Application Data

[63] Continuation of application No. 07/393,618, Aug. 14, 1989, abandoned, which is a continuation of application No. 06/657,091, Oct. 2, 1984, Pat. No. 4,935,370, and a continuation-in-part of application No. 06/564,962, Dec. 23, 1983, abandoned.

[51] Int. Cl.$^6$ .............................. C12P 21/00; C12P 21/02
[52] U.S. Cl. ....................... 435/69.1; 435/69.4; 435/320.1
[58] Field of Search ................................. 435/69.1, 69.4, 435/91, 172.3, 252.33, 320.1, 91.1; 536/23.51, 23.2; 935/44, 45, 46

[56] References Cited

U.S. PATENT DOCUMENTS

| | | | |
|---|---|---|---|
| 4,332,892 | 6/1982 | Ptashne et al. | 435/69.7 |
| 4,349,629 | 9/1982 | Carey et al. | 435/172.3 |
| 4,582,800 | 4/1986 | Crowl | 435/69.51 |
| 4,666,847 | 5/1987 | Alford et al. | 435/252.33 |

FOREIGN PATENT DOCUMENTS

| | | |
|---|---|---|
| 0035384 | 9/1981 | European Pat. Off. |
| 0036776 | 9/1981 | European Pat. Off. |
| 0052002 | 5/1982 | European Pat. Off. |
| 0054330 | 6/1982 | European Pat. Off. |
| 0067026 | 12/1982 | European Pat. Off. |
| 0068646 | 1/1983 | European Pat. Off. |
| 0068691 | 1/1983 | European Pat. Off. |
| 0047600 | 3/1983 | European Pat. Off. |
| 0073029 | 3/1983 | European Pat. Off. |
| 0075444 | 3/1983 | European Pat. Off. |
| 0077109 | 4/1983 | European Pat. Off. |
| 0089676 | 9/1983 | European Pat. Off. |
| 0103395 | 3/1984 | European Pat. Off. |
| 0104920 | 4/1984 | European Pat. Off. |
| 0114507 | 8/1984 | European Pat. Off. |
| 0121569 | 10/1984 | European Pat. Off. |
| 2073245 | 10/1981 | United Kingdom . |
| 2100737 | 1/1982 | United Kingdom . |
| 2091271 | 7/1982 | United Kingdom . |
| 8304030 | 11/1983 | WIPO . |

OTHER PUBLICATIONS

Nishimori et al., "Cloning in *Escherichia coli* of the Structural Gene of Prorennin, the Precursor of Calf Milk–Clotting Enzyme Rennin", J. Biochem. 90:901–904 (1981).
Nishimori et al., "Nucleotide Sequence of Calf Prorennin cDNA Cloned in *Escherichia coli*", J. Biochem. 91:1085–1088 (1982).
Nishimori et al., "Expression of cloned calf prochymosin gene sequence in *Escherichia coli*", Gene, 19:337–344 (1982).
Harris et al., "Molecular cloning and nucleotide sequence of cDNA coding for calf preprochymosin", Nucl. Acids Res., 10:2177–2187 (1982).
Guarante et al., "Improved Methods for Maximizing Expression of a Cloned Gene: a Bacterium That Synthesizes Rabbit β–Globin", Cell, 20:543–553 (1980).
Emtage et al., "Synthesis of calf prochymosin (prorennin) in *Escherichia coli*", Proc. Natl. Acad. Sci., 80:3671–3675 (1983).
Miller et al., "Molecular Cloning of DNA Complementary to Bovine Growth Hormone mRNA", J. Biol. Chem., 255, 7521–7524 (1980).
Woychik et al., "Cloning and nucleotide sequencing of the bovine growth hormone gene", Nucl. Acids Res., 10:7197–7210 (1982).
Keshet et al., "Cloning of bovine growth hormone gene and its expression in bacteria", Nucl. Acids Res. 9:19–30 (1981).
Seeburg et al., "Efficient Bacterial Expression of Bovine and Porcine Growth Hormones", DNA 2:37–45 (1983).
Goeddel et al., "Direct Expression in *Escherichia coli* of a DNA sequence coding for human growth hormone", Nature 281:544–548 (1979).
Bertrand et al., "New features of the regulation of the tryptophan operon", Science 189:22 (1975).
DeBoer et al., "Portable Shine–Dolgarno regions—a system for a systematic study of defined alterations of nucleotide sequences within *E. coli* ribosome binding sites", DNA 2:231 (1983).
Roberts et al., "A general method for maximizing the expression of a cloned gene", Proc. Natl. Acad. Sci. USA 76:760 (1979).
Gene Expression, vol. 2, Eucaryotic Chromosomes, Lewin, 1974, John Wiley & Sons, London, pp. 148–153.
Novick et al., "Uniform nomenclature for bacterial plasmids: a proposal", Bacteriological Reviews, 40:168 (1976).
Nishi et al., "Construction and Application of a Novel Plasmid 'ATG Vector' for Direct Expression of Foreign Genes in *Escherichia coli*", DNA, vol. 2, No. 4:265–273 (1983).
Nishimori et al., J. Biochem., 90, 901–904 (1981).
Nishimori et al., J. Biochem., 91, 1085–1088 (1982).
Nishimori et al., Gene, 19, 337–344 (1982).
Harris et al., Nucl. Acids Res., 10, 2177–2187 (1982).
Guarante et al., Cell, 20, 543–553 (1980).
Emtage et al., Proc. Natl. Acad. Sci., 80, 3671–3675 (1983).

*Primary Examiner*—James Martinell
*Attorney, Agent, or Firm*—Peter C. Richardson; Gregg C. Benson

[57] ABSTRACT

Promoter-ribosome binding site (rbs) expression elements of general utility for high level heterologous gene expression; plasmids carrying said promoter-rbs expression elements and encoding genetic information for direct high level expression in bacteria of heterologous proteins, especially plasmids carrying a gene coding for prorennin or mammalian growth hormones; methods for their construction, including the use of synthetic linkers to provide desirable functional properties thereto; recombinant microorganisms comprising said plasmids; expression of said bacterial produced heterologous proteins by said recombinant microorganisms; and demonstration of the activities of the thus-produced proteins.

24 Claims, 10 Drawing Sheets

|          |     | Sequence |     |     |     |     |     |     | Spacing |
|----------|-----|----------|-----|-----|-----|-----|-----|-----|---------|
| Plasmid  | SD  |          |     |     |     |     |     |     |         |
| pPFZ-R2  | TAA | AAA | GGA | GAA | TTC |     |     | ATG | 5bp |
| pPFZ-R4  | TAA | AAA | GGG | TAT | CGA | GAA | TTC | ATG | 11bp |

*FIG. 4*

EXPRESSION PLASMIDS FOR IMPROVED PRODUCTION OF HETEROLOGOUS PROTEIN IN BACTERIA

CROSS-REFERENCE TO RELATED APPLICATION

This application is a continuation of application Ser. No. 393,618, filed Aug. 14, 1989, now abandoned, which is a continuation of Ser. No. 06/657,091, filed Oct. 2, 1984, now U.S. Pat. No. 4,985,370, and a continuation-in-part of application Ser. No. 564,962, filed Dec. 23, 1983 now abandoned.

BACKGROUND OF THE INVENTION

1. Field of the Invention

This invention relates to recombinant DNA technology for expressing heterologous proteins in bacteria. More particularly it relates to methods and means for efficient direct expression of prochymosin and mammalian growth hormones in *Escherichia coli*.

2. Description of the Prior Art

Calf rennin (chymosin) the preferred milk-clotting protease for use in cheese production is in short supply. Alternative milk-clotting agents; namely, fungal proteolytic enzymes have been developed. However, because of their great proteolytic activity, they tend to reduce the yield of cheese and often give bitter flavors.

The economic attractiveness of a steady and sufficient supply of a milk-clotting protease has led several investigators to apply recombinant DNA technology to the problem. Nishimori et al., J. Biochem. 90:901–904 (1981) report cloning of the structural gene of prorennin (prochymosin) in *E. coli*. In a subsequent publication, Nishimori et al., J. Biochem. 91:1085–1088 (1982), reported the nucleotide sequence of calf prorennin cDNA which they had cloned in *E. coli*. Construction of an expression plasmid having the lacUV promoter and its ability to produce a fused protein containing almost all of the prochymosin peptide joined to the short N-terminal peptide of *E. coli* beta-galactosidase is described by Nishimori et al., Gene 19:337–344 (1982).

European Patent Application 73,029 published Mar. 2, 1983 describes calf prorennin DNA-containing plasmids, microorganisms (*E. coli*) transformed with said plasmids, and their expression of prorennin.

British Patent Application 2,091,271A, published Jul. 28, 1982, discloses methods and agents for producing rennin, prorennin and preprorennin, including the use of various promoters (lac, trp, ura3, etc.) to obtain expression. One of the disclosed DNA sequences that codes for preprorennin has attached to it a transcriptional promoter and a ribosomal binding site at the 5'-end. The distance between the beginning of the DNA which codes for preprorennin and the DNA segment carrying the transcriptional promoter and ribosomal binding site is varied.

British Patent Application 2,100,737A, published Jan. 6, 1983, describes recombinant DNA technology for producing chymosin, methionine chymosin, prochymosin, methionine prochymosin and preprochymosin. Vectors carrying an *E. coli* trp promoter-operator fragment and a transcription terminator, an initiation codon and a Shine-Dalgarno (SD) sequence which serves as a ribosome binding site are disclosed. Investigation of the effect of spacing between the SD and ATG sequences is also disclosed.

European Patent Application 77,109, published Apr. 20, 1983, describes DNA molecules, i.e., plasmids, comprising genes for preprochymosin and specific DNA sequences such as a double lac UV5 or a modified trp system, and their use to transform microorgamisms (lactobacilli, streptococci, bacillus or yeast) to generate transformants which produce preprochymosin in its allelic and maturation forms.

European Patent Application 36,776, published Sep. 30, 1981 describes expression vectors having the trp promoter-operator from which the attenuation region has been deleted, and methods for their production. Transformants carrying said vectors can be grown up in tryptophan-rich media so that cell growth proceeds uninhibited by premature expression of heterologous peptide encoded by an insert otherwise under control of the trp promoter-operator system.

Emtage et al., Proc. Natl. Acad. Sci. 80:3671–3675, 1983 and Japanese Patent Application No. SHO 58-38,439, filed Mar. 9, 1983, communicated to us by Beppu, describe construction of hybrid plasmids carrying prochymosin cDNA and containing the *E. coli* trp operon and the use thereof for expression of prorennin at levels greater than those reported by prior investigators A further communication from Beppu disclosed an amendment to said Japanese application, said amendment being filed on Nov. 15, 1983. The amendment relates, in part, to the effect of variation in the distance separating the SD sequence from the initiation codon for prochymosin, and the effect of replacing the N-terminal amino acids of prochymosin by peptides of varying length.

Harris et al., Nucleic Acids Research 10:2177–2187 (1982) report the cloning and nucleotide sequence of cDNA coding for preprochymosin. Goff et al., Gene 27, 35–46 (1984) describe the expression of calf prochymosin in *Saccharomyces cerevisiae*, a yeast. The restriction endonuclease cleavage map and DNA sequence of preprochymosin cDNA have been published Nishimori et al., J. Biochem., 91:1085–1088, (1982).

Mammalian growth hormones, including human epidermal growth factor (h-EGF), are of considerable interest because of their potential to improve animal husbandry. Their general use has been restricted because of their very limited availability. The economic attractiveness of an adequate supply of said hormones has led several investigators to apply recombinant DNA technology to the problem.

Human epidermal growth factor (EGF) or urogastrone is not only a stimulator of epidermal tissue growth but is also a potent inhibitor of gastric acid secretion. The full potential of EGF has not been investigated primarily because of lack of sufficient material.

The use of recombinant DNA methodology for the manufacture, cloning and expression of a structural gene for urogastrone and of genes for polypeptide analogs thereof are described in International Patent Application No. 83/04030, published Nov. 24, 1983.

The cloning of DNA complementary to bovine growth hormone mRNA, the nucleotide sequence thereof and the corresponding amino acid sequence predicted therefrom are reported by Miller et al., in European Patent Application 47,600, published Mar. 17, 1983 and J. Biol. Chem. 255, 7521–7524 (1980), and by Woychik et al. in Nucleic Acids Research 10, 7197–7210 (1982). British Patent Application 2,073,245A, published Oct. 14, 1981, and Kesket et al., Nucleic Acids Research 9, 19–30 (1981) describe the cloning of bovine growth hormone and its expression in *E. coli* HB101 as a fused beta-lactamase-bovine growth hormone protein.

Processes for expressing bovine growth hormone gene, plasmids and plasmid hosts for use therein are disclosed in European Patent Applications 67,026 and 68,646, published Dec. 15, 1982 and Jan. 5, 1983, respectively. Each application discloses E. coli as the host organism. The latter application, the counterpart of U.S. Pat. No. 4,443,539 issued Apr. 17, 1984, also divulges Saccharomyces cerevisiae as host organism.

Seeburg et al., DNA, 2 37–45 (1983) report the cloning in bacteria of cDNAs prepared using poly (A)mRNA from bovine or porcine pituitaries and the construction of expression vectors thereform which achieved efficient bacterial production of the mature animal (bovine or porcine) growth hormones. The technique adopted was analogous to that previously described by Goeddel et al., Nature, 281, 544–548 (1979) for direct expression of human growth hormone in E. coli. In each instance the bacterial expression vectors used were under control of the E. coli trp promoter. European Patent Applications Nos. 103,395 and 104,920, published Mar. 21, 1984 and Apr. 4, 1984, describe production of bovine growth hormone-like polypeptide and production of swine growth hormone-like polypeptides, respectively via recombinant DNA methodology.

Administration of bovine growth hormone to dairy cows increases milk production and improves the feed intake to milk output ratio [Macklin, J. Dairy Science 56, 575–580 (1973)]. European Patent Application 85,036A, published Aug. 3, 1983, discloses that biosynthetically produced (by rDNA) bovine growth hormone and/or fragments of it also increase milk production in cows and production of meat, wool, eggs and fur in pigs and other farm animals.

U.K. Patent Specification 1,565,190, published Apr. 16, 1980, discloses recombinant plasmid vectors capable of transforming microorganims and containing within their nucleotide sequences subsequences which code for the growth hormone of an animal species. U.S. Pat. No. 4,237,224 describes plasmid vectors for introducing foreign DNA into unicellular organisms.

Plasmids having a HindIII insertion site for a chosen eukaryotic DNA fragment, said site being adjacent to a bacterial promoter such as the trp promoter, wherein the transcription and translation of the DNA fragment are controlled by the promoter, are described in U.S. Pat. No. 4,349,629.

The level of expression of a cloned gene is influenced by a number of factors such as the number of gene copies and the efficiency of transcription and translation. Efficient transcription of an inserted gene requires the presence of a strong promoter and efficient translation requires the presence of a suitable ribosome binding site in the mRNA and appropriate spacing between the rbs and the translation initiation codon. The promoter precedes that portion of the DNA (structural gene) which codes for a protein. The ribosome binding site (rbs), or ribosome recognition sequence, is believed to consist of a sequence at least 3–9 bp long, known as the Shine-Dalgarno (SD) sequence. It begins 3 to 11 bp upstream from the AUG which encodes the amino terminal methionine of the protein [Guarante et al., Cell 20:543–553, (1980)], and is complementary to the 3'-terminal sequence of 16S RNA.

The separation of the promoter from the translational start signal (AUG) for a gene can markedly affect the levels of protein produced (Guarante et al., loc. cit. and references cited therein). This reference and Ptashne et al., U.S. Pat. No. 4,332,892 issued Jun. 1, 1982 describe the effects of placing a "portable promoter" fragment at varying distances from the 5'-end of a gene upon expression.

Other references relevant to the effect of defined alterations of nucleotide sequences and especially of variations between the SD region and the start codon are: Scherer et al., Nucl. Acids Res. 8:3895–3907 (1980); Shepard et al., DNA 1:125–131 (1982); Windass et al., Nucl. Acids Res. 10:6639–6657 (1982); De Boer et al., DNA 2:231–235 (1983); Tacon et al., Molec. gen. Genet. 177, 427–438 (1980); and Itoh et al., DNA 3, 157–165 (1984).

SUMMARY OF THE INVENTION

This invention relates to a promoter-rbs expression element of general utility for high level heterologous gene expression, to expression plasmids carrying said expression element for direct expression of heterologous proteins (prokaryotic or eukaryotic) and which, when introduced into competent bacteria, produce recombinant microorganisms capable of expressing unexpectedly and surprisingly high levels of said proteins; to methods for their construction; recombinant E. coli, especially transformants, comprising said plasmids; and the use of said recombinant microorganisms to produce said heterologous proteins. More particularly it relates to high level expression by E. coli of heterologous genes encoding for proteins such as prochymosin and mammalian growth hormones such as bovine and porcine growth hormones and human epidermal growth factor and especially to expression plasmids useful therefor. Said plasmids comprise a selectable marker; a replicon, i.e., a DNA sequence which comprises a region to control autonomous replication in the host cell; and the E. coli trp promoter joined to said heterologous protein cDNA sequence (gene) by a synthetic DNA linker, said plasmid comprising a novel ribosome binding region which may be of variable length. A feature of the plasmids of this invention is the presence, in the ribosome binding region upstream from the ATG initiation codon, of the nucleotide sequences 5' TAAAAAG-GAGAATTC ATG 3' or 5' TAAAAAGGGTATC-GAGAATTC ATG 3'. A preferred expression plasmid of this invention has the additional and significant feature of a translational stop codon (TAA) in the same reading frame as the protein coding sequence just prior to the Shine-Dalgarno sequence.

The state of the art of molecular biology is at a sufficiently developed level such that in vitro construction of hybrid plasmids which should express a given protein or polypeptide is possible from a knowledge of the cDNA sequence which encodes said polypeptide and the restriction endonuclease cleavage-map of said sequence. However, despite this, there is no basis in the art to suggest that a particular, and even critical, arrangement of the DNA sequence within a plasmid will, when suitably introduced into a microorganism, afford significant and unexpectedly high expression of the polypeptide.

The herein described recombinant microorganisms express heterologous proteins in significantly greater yields than do previously described microorganisms and achieve, for the first time, their economic production via recombinant DNA technology.

As those skilled in the art will recognize, recombinant microorganisms can be produced by a number of methods, e.g. transformation, transduction, conjugation or transfection. It is, therefore, intended to include in the term "recombinant microorganisms" microorganisms which are capable of expressing the herein described heterologous proteins whenever said microorganisms are prepared by any of the above-mentioned methods. To put it another way, the definition of recombinant microorganism as used herein includes any microorganism capable of expressing the heterologous protein of a heterogenic or xenogenic sequence whenever said microorganism is prepared by recombinant techniques.

Another object of this invention comprises the nucleotide sequences described herein for the ribosome binding site of a gene encoding a prokaryotic or eukaryotic protein which when inserted into a bacterial plasmid downstream from a transcriptional promoter sequence affords efficient expression in E. coli. The ribosome binding site regions described contain a convenient EcoRI restriction endonuclease cleavage site just upstream from the ATG initiation codon, providing for a method for inserting any DNA fragment containing a protein translational start codon into the expression vectors behind the SD sequence. In other words, the gene in the expression plasmids described herein could be any gene coding for a prokaryotic or eukaryotic protein. For example, the herein described nucleotide sequences between the ribosome binding site and ATG initiation codon afford high expression of cDNA sequences, such as, prochymosin (prorennin), bovine growth hormone, porcine growth hormone, and human epidermal growth factor (urogastrone). The proteins, bovine and porcine growth hormones and human epidermal growth factor, are collectively referred to herein as mammalian growth factors.

Bacterial production of a particular heterologous gene can result in a polypeptide which may or may not have a methionine residue at the amino terminus of said polypeptide. Therefore, the term "prochymosin" (prorennin) as used herein is intended to include methionine prochymosin (prorennin) and prochymosin (prorennin). The same applies to the other polypeptides described herein. Further, when reference to "chymosin" (rennin) is made herein it is intended to include within said term the known allelic forms thereof (e.g. A, B, etc.).

The following examples are intended to illustrate more fully the nature of the invention without acting as a limitation upon its scope.

BRIEF DESCRIPTION OF THE DRAWINGS

FIG. 4 presents the nucleotide sequence and spacing between the ribosome binding site and initiation codon (ATG) of the prochymosin (prorennin) gene for each of plasmids pPFZ-R2 and pPFZ-R4. This is the only region in which said plasmids differ in nucleotide sequence.

DETAILED DESCRIPTION OF THE INVENTION

The Microorganisms

Figure 1:
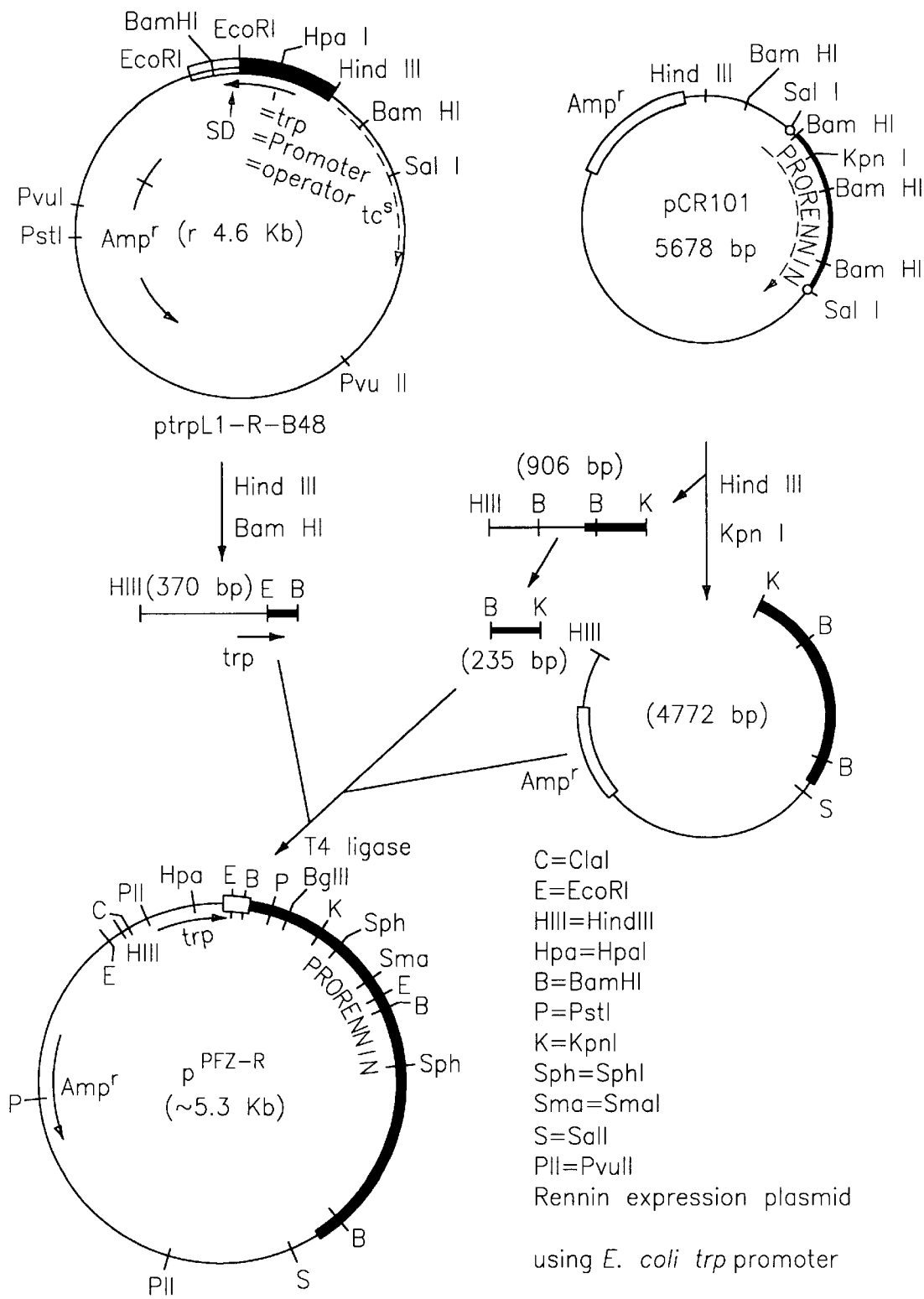
FIG. 1 presents the overall scheme for construction of plasmids pPFZ-R2 and R4 (pPFZ-R), including the restriction map of said plasmids which is common to each of pPFZ-R2 and R4. The arrow indicates the direction of expression from the trp promoter sequence into the prochymosin (prorennin) gene (represented by the heavy segment). The synthetic insert is represented by the open box.

The microorganisms and recombinant microorganisms used and/or produced in this invention and the depositories from which they are available are listed below:

E. coli C600, also known as CR34, ATCC 23724
E. coli HB101 NRRLB-11371, ATCC-33694
E. coli MM294 ATCC-33625
E. coli W3110 ATCC-27325
E. coli HB101 comprising pPFZ-R2 ATCC-39544
E. coli HB101 comprising pPFZ-R4 ATCC-39543

As those skilled in the art will recognize, any transformable E. coli K-12 strain can be used in this invention as host organism in place of those enumerated above. Further, protease negative strains of E. coli will, as the skilled artisan appreciates, afford equal or better results than the above-mentioned E. coli strains.

The above-identified recombinant microorganisms ATCC 39543 and 39544 were deposited on Dec. 14, 1983 under the terms of the Budapest treaty in the American Type Culture Collection, Rockville, Md., a recognized depository affording permanence of the deposits and ready accessibility thereto by the public if a patent is granted on this application. They were given the accession numbers shown above. The deposits are available during pendency of this application to one determined by the Commissioner of the United States patent and Trademark Office to be entitled thereto under 37 CFR 1.14 and 35 USC 122, and in accordance with foreign patent laws in countries wherein counterparts of this application, or its progeny, are filed. All restrictions on the availability to the public of the microorganism deposited will be irrevocably removed upon granting of the patent.

Preparation of RNA and Cloning of cDNA

Total RNA from animal pituitaries was obtained from a local slaughterhouse and was isolated by the procedure of Ullrich et al., Science 196, 1313–1319 (1977). Polyadenylated RNA was obtained from total RNA by chromatography on oligo(dT)cellulose. Double-stranded cDNA was prepared from this RNA and a size fraction of the cDNA was cloned by standard methods in *E. coli* using plasmid pBR322 and the homopolymer method as described previously (Miller, W., et al. 1980, J. Biochem., 255, 7521, Goeddel et al., 1979; Nature 281, 544–548; Seeburg et al., 1983, DNA 2, 37–45).

Colonies transformed with cDNA containing plasmids were replica plated onto nitrocellulose filters. Filters containing transformant colonies were processed for hybridization according to the procedure described by Grunstein and Hogness (1975, Proc. Natl. Acad. Sci. 72, 3961–3965). Radioactively labeled synthetic oligonucleotides whose sequence was derived from published cDNA sequences were used as probes for detecting the cloned cDNAs. Hybridizing colonies were grown in 5 ml. LB, and plasmid DNAs prepared and cloned sequences characterized by cleavage with restriction endonucleases followed by electrophoresis of DNA fragments in gels.

The Starting Plasmids

Plasmid, pCR101 is described by Nishimori et al., Gene, 19:337–344 (1982). It carries the full-length cDNA of prochymosin, the gene for ampicillin resistance, and consists of 5678 bp. It includes a cleavage site for HindIII and several BamHI sites.

Plasmid ptrpLI is described by Edman et al., Nature 291:503–506 (1981), and plasmid pBR322 by Bolivar et al., Gene 2:95–113 (1977).

Materials

Restriction endonucleases (AsuI, BamHI, EcoRI, HindIII, ClaI, HinfI, KpnI, PstI, PvuII, RsaI, SalI), T4 ligase, and DNA polymeraseI (large fragment) were purchased from New England Biolabs, T4 polynucleotide kinase from PL Biochemicals, bacterial alkaline phosphatase from Bethesda Research Laboratories (BRL), calf intestine alkaline phosphatase from Boehringer Corp. All enzymes were used under conditions recommended by the supplier. Radiochemicals were purchased from New England Nuclear (NEN). Protein molecular weight standards were purchased from BRL, purified bovine chymosin was purchased from Sigma Chemical Company (Sigma) and purified bGH from Miles.

Bacteria were grown routinely at 37° C. in L Broth or on L-agar plates (Miller, J. Experiments in Molecular Genetics, Cold Spring Harbor Laboratory, New York, p. 433, 1972) containing either ampicillin (25 μg/ml) or tetracycline (10 μg/ml). For large scale plasmid preparation, log phase cultures were amplified by the addition of chloramphenicol (170 μg/ml) [Clewell and Helinski Helsinki, J. Bacteriol. 110:1135 (1972)].

The plasmid pBGH-7 comprises a pBR-322 that contains a full length cDNA of bGH cloned into the PstI site and was prepared as described by Miller, W. et al., J. Biochem. 255, 7521 (1980). The cloned cDNA contains approximately 830 bp including 31 bp of the 5' untranslated sequence, the entire pre-hormone structural sequence (651 bp), the entire 3' untranslated region (104 bp), a brief stretch of poly(A), and the dC-dG tails. The plasmid pGH-24 comprises a pBR322 that contains a full length cDNA of pGH cloned into its PstI site and was prepared by methods similar to those described by Seeburg et al. DNA 2, 37–45 (1983). The pGH-24 plasmid DNA was constructed and provided by Dennis Pereira. The plasmid pBR-322 was previously described by Bolivar et al. Gene 2, 95–113 (1977).

Synthesis of Oligonucleotides

Synthetic oligonucleotides 5'.AGAATTCATGG.3' (I) and 5'.CCATGAATTCT.3' (II) were chemically synthesized by the phosphite method [Caruthers, J. Am. Chem. Soc. 103, 1385 (1981)] and were purified from 6M urea-20% polyacrylamide gels.

The 18-bp and 22-bp single stranded oligomers were synthesized by methods described herein and were transformed to a 40-mer adapter also as described herein. Double stranded 40-mer is produced by annealing and ligating the single stranded 18- and 22-mers according to known procedures.

The oligonucleotides used for pGH and bGH were synthesized via the phosphoramidite procedure of Caruthers et al, Tetrahedron Lett. 24, 245 (1983) and fragments were synthesized from single-stranded oligomers 11–16 bases long.

Molecular Cloning Reactions

The fill-in reaction of recessed 3' ends of double-stranded DNA using Klenow fragment of *E. coli* DNA polymerase I was essentially as described by Maniatis et al. [Molecular Cloning, A Laboratory Manual, Cold Spring Harbor Laboratory p. 113 (1982)]. The transfer of the gamma-phosphate of ATP to the 5'-OH terminus of the synthetic linker DNA by T4 polynucleotide kinase was as described by Maniatis (ibid.). About 2 μg of double stranded linker DNA was phosphorylated in a 20 μl reaction mixture containing 70 mM Tris (pH 7.6), 10 mM MgCl$_2$, 5 mM dithiothreitol (DTT), 20 μCi [gamma-32P]ATP (5000 Ci mmol$^{-1}$; NEN), T4 polynucleotide kinase (10 units) was added and the reaction allowed to proceed at 37° C. for 15 minutes; 1 μl of 10 mM ATP and 10 units of T4 kinase were then added and the reaction allowed to proceed for an additional 30 minutes at 37° C. The kinased linkers were stored at -20° C.

When necessary the terminal 5' phosphates were removed from DNA by treatment either with bacterial alkaline phosphatase (BAP) or with calf intestinal alkaline phosphatase (CIP) [Chaconas et al. Methods Enzymol. 65:75 (1980)]. Briefly, in the CIP treatment, the plasmid DNA was digested to completion with the appropriate restriction enzyme(s) and precipitated in ethanol. The DNA pellet was resuspended in CIP reaction buffer (0.1M glycine, 1 mM MgCl$_2$, 0.1 mM ZnCl$_2$, pH 10.4) at a final concentration of 1 μg per 10 μl buffer. The sample was heated to 65° C. for 10 minutes, then cooled on ice for 5 minutes. The calf intestinal alkaline phosphatase was then added to a final concentration of 0.5 units of enzyme per 1 μg of DNA. The mixture was incubated at 37° C. for 30 minutes followed by phenol-chloroform extraction, and ethanol precipitation of DNA fragments. The DNA pellet was resuspended in distilled water to a final concentration of 100 μg/ml.

In the case of BAP treatment, the plasmid DNA was cleaved with the restriction endonuclease(s) of choice and precipitated in ethanol. The DNA pellet was resuspended in buffer (50 mM NaCl, 10 mM MgCl$_2$, 10 mM Tris, 10 mM DTT) at a final concentration of 1 μg per 10 μl of buffer. The reaction mix was heated to 65° C. for 10 minutes and quenched on ice. The bacterial alkaline phosphatase was added to a final concentration of 50 units of enzyme per 1 μg of DNA. The reaction mixture was incubated at 65° C. for 2 hours followed by phenol-chloroform extractions, and ethanol precipitation of the DNA fragments.

The construction of the bacterial expression plasmids involved manipulations that joined DNA fragments from various plasmids. All steps are shown in the accompanying Figures. Generally, DNA fragments were purified following isolation from gels and ligated to other fragments or plasmid DNA in 20–50 μl of 66 mM Tris-HCL (pH 7.6), 5 mM MgCl2, 1 mM ATP, 20 mM DTT and 1 μl T4 ligase (400 units). Competent cells of E. coli were prepared and transformed with one half of the ligation mixture using standard procedures [Mandel et al., J. Mol. Biol. 53, 1543 (1970).

DNA Sequence Determination

DNA sequences were established by the chemical degradation method [Maxam, A. and Gilbert, W. Methods Enyzmol. 65:499–560 (1980)] utilizing end-labeled DNA fragments. Each ribosome binding site region was independently sequenced several times on both strands.

Preparation of Plasmid DNA

Large scale preparations of plasmid DNA were prepared by the alkaline-SDS procedure previously described [Birnboim, et al., Nucleic Acid Res. 7:1513 (1979)] followed either by ethidium bromide-CsCl buoyant density centrifugation or fractionation on a Biogel A-50 (BioRad) column as described by El-Gewely et al., [Anal. Biochem. 102:423–428 (1980)]. Miniprep amounts of DNA were prepared by a rapid modification of the alkaline-SDS procedure [Birnboim et al., Ibid.].

Gel Electrophoresis

Agarose slab gels, 0.7% to 1% were run according to the conditions described by Maniatis et al. (loc. cit., p. 150–164). Gels were stained for 15 minutes with 1 μg/ml ethidium bromide and photographed under illumination from 266 nm U.V. light using Polaroid film (Type 57, ASA 3000) with a Kodak Wratten filter (23 A).

Acrylamide gels (20×15×0.15 cm) of 5% to 12.5% were used to identify small (less than 1.5 kb) restriction fragments according to the method described by Maniatis et al., [Biochemistry 14:3787–3794 (1975)]. Gels were stained and photographed as for agarose gels.

DNA fragments were purified from gel slices by electroelution in a dialysis bag containing 0.1×TBE (8.9 mM Tris-borate, 8.9 mM boric acid, 0.2 mM EDTA). Identification of Heterologous Protein Produced in E. coli Bacterial cultures containing pBR322 or the expression plasmids (pPFZ-R2 or pPFZ-R4) were grown overnight in LB broth or M9CA medium (Maniatis et al., loc. cit.) containing 4 μg/ml thiamine, 25 μg/ml ampicillin, and 100 μg/ml tryptophan. These cultures were diluted 1:25 into M9CA medium (Maniatis et al. loc. cit., without tryptophan to allow complete induction of the trp promoter), or M9CA medium plus 100 μg/ml tryptophan (to inhibit induction of the trp promoter), or LB medium (for a negative control), and grown in shaker flasks to cell densities of $A_{560}$=1.0. For total cell protein extraction, cell pellets equivalent to 200 μl culture were lysed in 2% sodium dodecyl sulfate (SDS), 1% β-mercaptoethanol, and protein was precipitated with 10 volumes of cold acetone. Precipitated protein was redissolved in SDS sample buffer and aliquots were electrophoresed on 10% or 12.5% SDS-polyacrylamide gels [Laemmli, Nature 227:680–685 (1970)]. For labeled protein preparation, cell pellets from 1 ml aliquots of expression cultures were suspended in 1 ml supplemented M9CA medium (M9CA salts, 0.2% glucose, 4 μg/ml thiamine, 20 μg/ml standard amino acids except methionine and tryptophan) plus 25 μg/ml ampicillin and 75 Ci $^{35}$S methionine (NEN; 970 Ci/mmol). After one hour incubation at 37° C., cells were pelleted and resuspended in 200 μl 10 mM Tris (pH 8.0) 1 mM NaEDTA, then placed on ice for 10 minutes following additions of lysozyme to 1 mg/ml, NP40 to 0.2 percent, and NaCl to 0.35M final concentration. The lysate was adjusted to 10 mM $MgCl_2$ and incubated on ice for 30 minutes with 50 μg/ml DNase I (Sigma). Insoluble material was removed by mild centrifugation and this pellet fraction was dissolved in SDS sample buffer. Supernatant samples were immunoprecipitated with rabbit anti-prorennin antibody (Nishimori et al, Gene 19, 337–344) and staphylococcal adsorbent (Pansorbin; Cal Biochem) as described by Kessler [J. Immunology 117:1482–1490 (1976)]. The samples were subjected to SDS polyacrylamide gel electrophoresis (Laemmli, loc. cit.) and enhanced (Enlightning; NEN) before fluorography at −75° C. with Kodak XAR-2 film and a Cornex Lightning Plus intensifying screen.

Quantitation of Expression Levels

Estimations of the amount of heterologous protein produced by expression cultures were determined by densitometer scanning of protein gels containing total protein extracts from bacterial cultures. Individual lanes of the SDS-polyacrylamide gel of total cell protein extracts were analyzed using a Beckman DU-8B densitometer gel scan. The dried-down Coomasie-blue stained SDS-polyacrylamide gel was scanned in each lane to determine the percent of the total cell protein in the heterologous protein band. A scan of the total cell protein from a control culture (containing the pBR322 vector) was used to determine the native protein content in the region of the gel corresponding to the size of the recombinant product. After correcting for the background peaks apparent in the control culture, the expression levels were estimated as a percent of the total cell protein. The protein gels were scanned at 579 nm. Results Construction of ptrpLI-R2 and ptrpLI-R4

Figure 2:
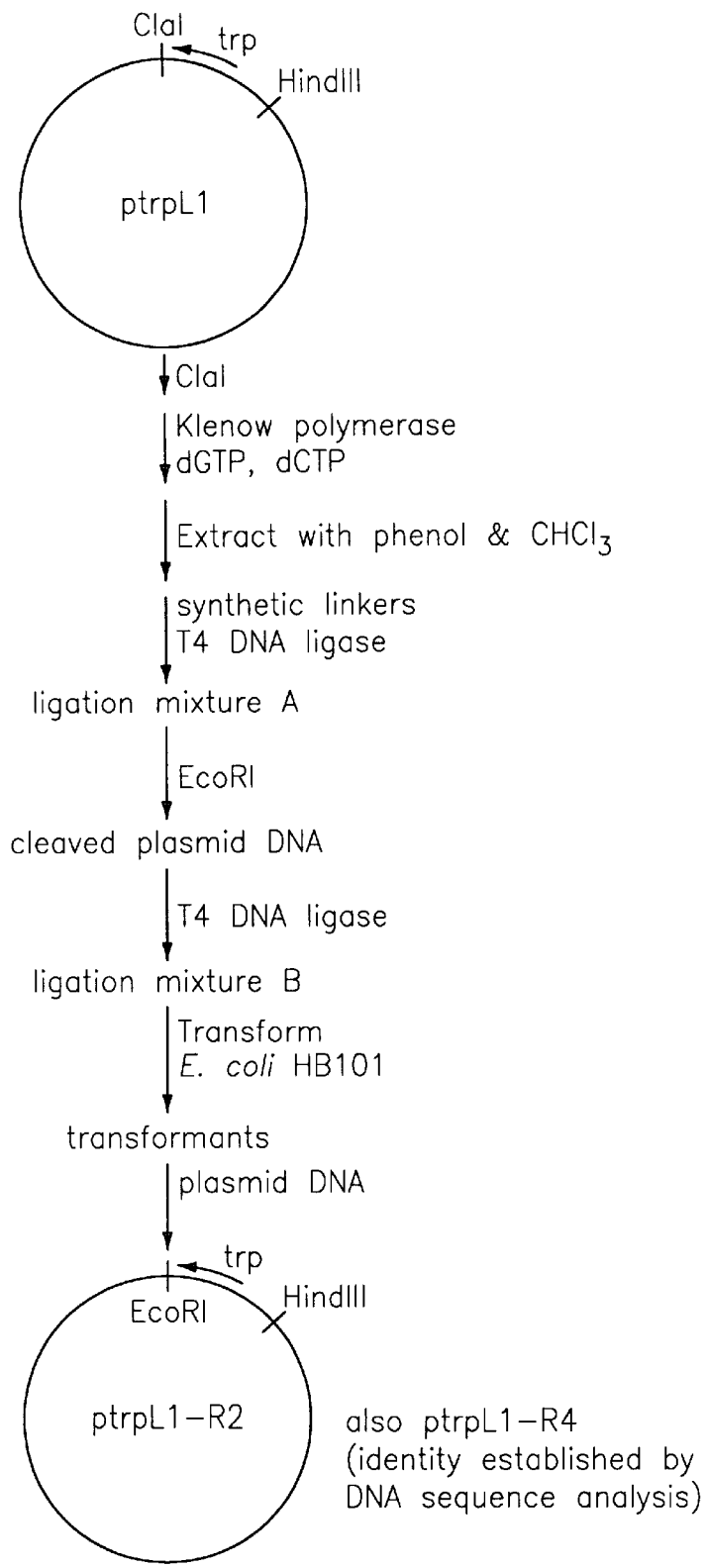
FIG. 2 depicts the scheme for construction of plasmids ptrpLI-R2 and R4.

The plasmid ptrpLI is a pBR322 derivative that contains part of the E. coli trp promoter operator and the Shine-Dalgarno (SD) sequence of trpl on a (~360 bp) HindIII-ClaI fragment. [Edman et al., Nature 291:503–506 (1981)]. This vector is, therefore, an expression plasmid with an unique ClaI cloning site adjacent to the trp regulatory region. Inserted DNAs must contain within their sequence an ATG translational initiation codon prior to the gene coding sequence which when inserted into ptrpLI will be properly spaced relative to the trpl ribosome binding site sequence. This expression vector was modified by inserting appropriate synthetic DNA linkers into the ClaI site as illustrated in FIG. 2.

A specific double stranded synthetic DNA linker was used to alter the nucleotide content around the ClaI restriction site of ptrpLI. About 10 μg of ptrpLI DNA was digested with 16 units of restriction endonuclease ClaI for 90 minutes at 37° C. The cohesive ends generated by the ClaI cleavage were blunted in a 100 μl reaction mixture containing 50 mM Tris-HCl (pH 7.2), 10 mM $MgSO_4$, 0.1 mM dithiothreitol, 0.2 mM dGTP, 0.2 mM dCTP. Klenow fragment of DNA polymerase (30 units) was added and the reaction allowed to proceed at 20° C. for 45 minutes. After phenol and chloroform extraction, the indicated phosphorylated deoxyoligonucleotide linker ~60 pmoles)

```
(5'  AGAATTCATGG  3')

(3'  TCTTAAGTACC  5')
``` was combined with ~1 μg (~0.6 pmoles) of the filled-in vector fragment and ethanol precipitated. These fragments were ligated at 4° C. for 18 hours in 30 μl of 66 mM Tris-HCl (ph 7.6), 5 mM $MgCl_2$, 1 mM ATP, 20 mM dithiothreitol and 800 units of T4 DNA ligase. The mixture was digested for 90 minutes with 3 units of EcoRI for 90 minutes. The EcoRI cleaved plasmid DNA was re-ligated at 4° C. for 4 hours in 100 μl of 66 mM Tris-HCl (pH 7.6), 5 mM $MgCl_2$, 1 mM ATP, 20 mM DTT, and 400 units of T4 DNA ligase. Competent cells of E. coli strain HB101 were transformed with 25 μl of the ligation mixture. [Mandel et al., J. Mol. Biol. 53:154 (1970)]. Plasmid DNA was prepared from 12 of the transformants and digested with EcoRI and HindIII. Ten of these plasmids contained the desired ~360-bp EcoRI-HindIII fragment. DNA sequence analysis verified that one of these plasmids (ptrpLI-R4) had the desired orientation of the synthetic linker and desired sequence at the junctions between the trp promoter and synthetic DNA.

During the DNA sequencing analysis of plasmid DNA from various transformants, it was discovered that one of the plasmids (ptrpLI-R2) had a 6-bp deletion in the region of the ribosome binding site. This deletion most likely resulted from the 3' to 5' exonuclease activity of the Klenow fragment of DNA polymerase I because the linker sequences are all present. It was recognized that this derivative had an altered ribosome binding site compared to the native trp SD sequence contained in ptrpLI-R4.

Cloning of the Synthetic Prorennin Adapter

The sequence of the synthetic double-stranded DNA used to modify the amino terminal end of prorennin is shown:

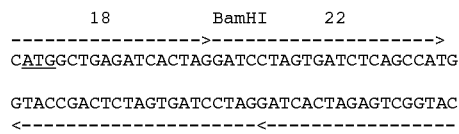

Figure 3:
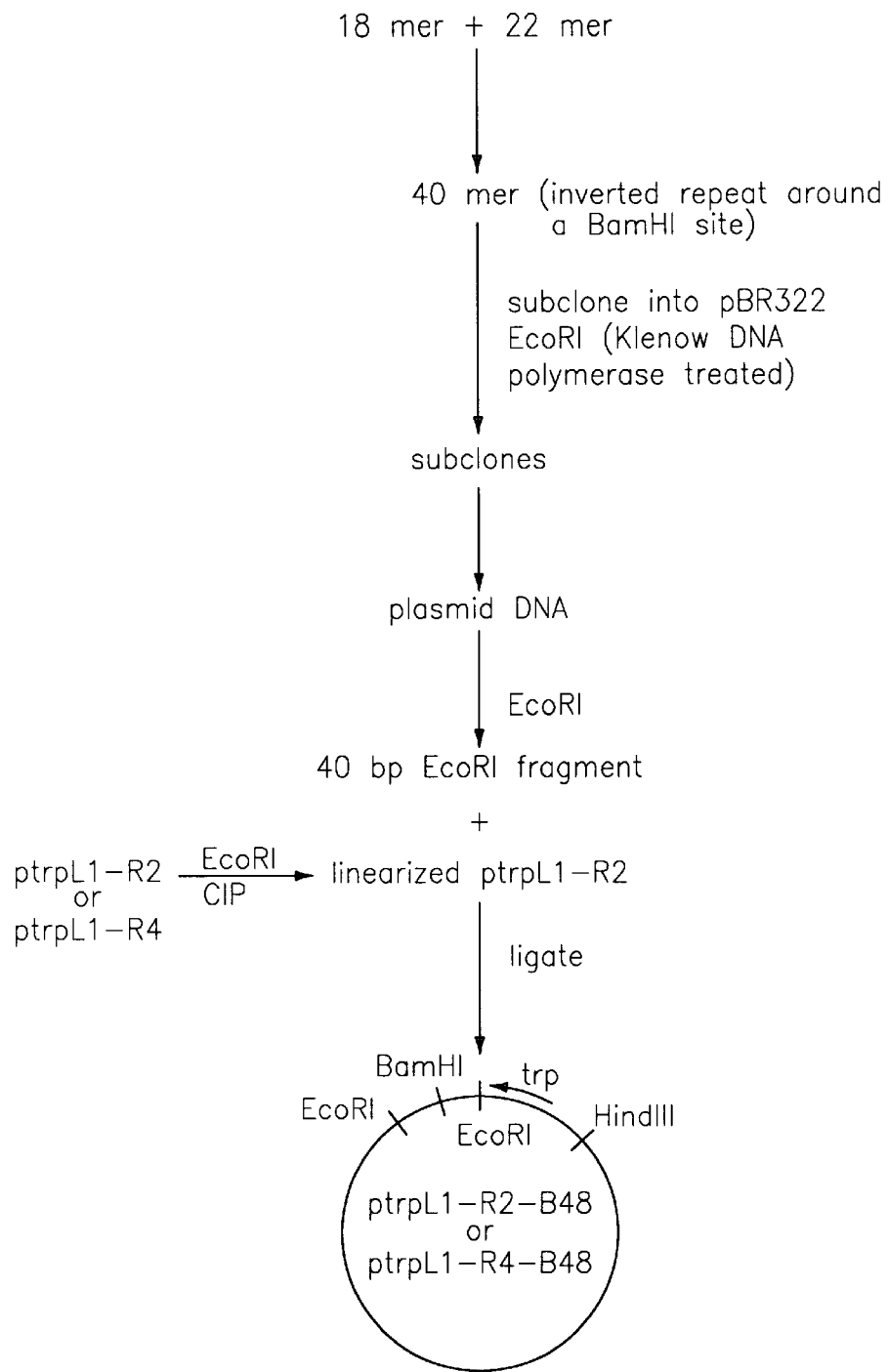
FIG. 3 presents the scheme for construction of plasmids ptrpLI-R2-B48 and ptrpLI-R4-B48.

This fragment was assembled from 2 single stranded oligomers, 18-bp and 22-bp long. This synthetic DNA encodes the artifical ATG initiation codon for protein synthesis and the first several codons of prorennin sequence [as reported by Nishimori et al., J. Biochem. 91:1085–1088 (1982)] in an inverted repeat around a BamHI site. This synthetic DNA was subcloned into the EcoRI restriction site of pBR322 that had previously been treated with the Klenow fragment of DNA polymerase I to fill in the cohesive ends. Subclones were identified by in situ colony hybridization of recombinant microorganisms using radioactively labeled 22-mer as probe [Grunstein, M. and Hogness, D., Proc. Natl. Acad. Sci. 72:3961 (1975)]. Plasmid DNA was prepared from 20 hybridization positive colonies and cleaved with BamHI or EcoRI to identify the subclone containing the desired plasmid. Approximately 100 μg plasmid DNA from recombinant microorganism #17 was cleaved with EcoRI and the 40 bp fragment was isolated on a 12.5% polyacrylamide gel. The purified 40 bp EcoRI fragment was inserted into the EcoRI sites of the 2 expression plasmid derivatives (ptrpLI-R2 and ptrpLI-R4) which had been previously cleaved with EcoRI and dephosphorylated by treatment with calf intestinal alkaline phosphatase. Plasmid DNA from several recombinant microorganisms of each ligation was prepared and digested with BamHI restriction endonuclease. Plasmids containing the 40 bp prorennin adapter inserted downstream from the trp expression sequence were identified by the presence of two BamHI sites approximately 700 bp apart. This construction scheme is illustrated in FIG. 3. These expression plasmids were referred to as ptrpLI-R2-B48 and ptrpLI-R4-B48.

These recombinant microorganisms were used as the source for an approximately 370 bp HindIII-BamHI DNA fragment containing the trp promoter-operator sequence, the ribosome binding site, the artifical ATG initiation codon, and the chemically derived sequence coding for the first 5 amino acid residues of prorennin. The nucleotide sequences downstream from the promoter, in the region of the ribosome binding site, differ due to the previous insertion of a different chemically synthesized deoxyoligonucleotide linker at the ClaI restriction site in the plasmid vector ptrpLI as described above. The resulting nucleotide content and spacing between the ribosome binding site (rbs) sequence and the ATG of the prorennin gene, and for other protein encoding genes disclosed herein, was shown by DNA sequence analysis to be as follows for each of the expression constructions:

| pPFZ(R) | 5'→3' | Spacing (bp) |
|---|---|---|
| R2 | AAGGAGAATTC ATG | 5 |
| R4 | AAGGGTATCGAGAATTC ATG | 11 |

Each ribosome binding site variation was used to make prorennin expression plasmids in order to later examine the possible effects that rbs nucleotide sequence content and spacing have on protein expression levels.

Construction of the Prorennin Expression Plasmids

The experimental steps used for constructing the prorennin expression plasmids are illustrated in FIG. 1. First, the 4772 bp vector fragment containing the plasmid replicon, the ampicillin resistance marker, and the desired prorennin coding sequence (from amino acid codon 83 to the stop (TGA) codon) was prepared by digesting 30 μg pCR101 plasmid DNA with HindIII and KpnI restriction endonucleases. The restriction reaction was electrophoresed on a 1% agarose gel and both DNA fragments were isolated from gel slices by electroelution. The 906-bp HindIII-KpnI fragment containing the amino terminal portion of the prorennin cDNA sequence was further digested by BamHI followed by electrophoresis on a 5% polyacrylamide gel. The 235-bp BamHI-KpnI fragment (encoding amino acid codons 6 to 83) was electroeluted from a gel slice.

The HindIII-BamHI DNA fragments containing the expression sequences from the different ptrpLI-R-B48 derivatives were separately mixed in approximately equal molar ratio with the two restriction fragments derived from pCR101 (4772 bp and 235 bp). The mixtures were ligated by addition of T4 DNA ligase and a portion of each ligation mix used for introduction into competent HB101 cells. Colonies were obtained in each instance when cells were selected on LB agar plates containing ampicillin (25 μg/ml). Several drug resistant colonies from the aforementioned colonies were picked into 5 ml LB cultures, and plasmid DNA was subjected to restriction enzyme analyses. In each group, most recombinant microorganisms were found to contain the complete prorennin gene recombined adjacent to the trp promoter-rbs sequence.

Restriction endonuclease analysis of these expression plasmids showed they contained the entire prorennin coding sequence properly aligned for direct expression of prorennin. DNA sequence analysis by the chemical degradation method of Maxam and Gilbert supra of most of the prorennin gene, the in vitro junction region and the trp promoter-operator region confirmed that the artificial initiation codon and the prochymosin coding sequence directly follows the E. coli trp promoter-operator and served to establish the separate identity of the two expression plasmids at the nucleotide level. The two prorennin plasmids constructed here have been designated as pPFZ-R2 and pPFZ-R4. Further, the ATG initiation codon follows the E. coli ribosomal binding site of the trp leader peptide by 5 and 11 nucleotides in expression plasmids pPFZ-R2 and pPFZ-R4, respectively.

Translation of the DNA sequence of these expression plasmids predicts a prorennin protein of 366 amino acids. The estimated molecular weight of such a polypeptide is about 41,000. When E. coli containing an expression plasmid is grown in minimal media lacking tryptophan, the cells produce a protein that migrates slightly larger than mature chymosin (about 36,000 daltons) in SDS-polyacrylamide gel electrophoresis [Laemmli, U. K. Nature 227:680 (1970)]. No such protein is produced by E. coli cells containing the vector plasmid pBR322 grown under identical conditions. Very little prorennin protein is produced by identical expression recombinants grown in M9CA media containing an abundance of tryptophan (100 µg/ml), implying that production in E. coli of the putative prochymosin protein is under control of the trp promoter-operator as designed.

Evaluation of Prorennin Synthesis by Expression Cultures

E. coli transformants carrying the prorennin expression plasmids pPFZ-R2 and pPFZ-R4 were grown in M9CA media lacking tryptophan for induction of the trp promoter. Cells were grown in shaker flasks to an $OD_{550}$ of 1.0. Cell pellets from these cultures were lysed in 2 percent SDS, 1 percent beta-mercaptoethanol, and proteins were precipitated with acetone. Precipitated proteins were redissolved in SDS sample buffer and aliquots were electrophoresed on 10 percent SDS-polyacrylamide gels [Laemmli, Nature 227:680 (1970)]. Prorennin levels were determined by densitometer gel scans of the Coomassie blue stained gel at 579 nm.

It has been observed by phase contrast microscopy that refractile inclusion bodies exist in E. coli cells containing the prochymosin expression plasmids. Control cells containing the plasmid vector pBR322 when grown under identical conditions reveal no such refractile inclusion bodies. Analogous observations have been reported with respect to genetically engineered microorganisms which produce exogenous gene products [Carrier et al., Trends in BioTechnology 1:109 (1983)], such as insulin and thymosin. The retractile bodies are considered to be pools of the expressed foreign protein.

The presence of refractile inclusion bodies appears to directly correlate with a high level of prorennin production.

The above-described bacterially synthesized prochymosin specifically reacts with prorennin anti-bodies.

Evaluation of the growth of recombinants of E. coli HB101 carrying plasmids pPFZ-R2 and pPFZ-R4 under identical shaker flask growth conditions showed that plasmid pPFZ-R2 reproducibly produced prorennin levels ranging from 10 to 15%, and pPFZ-R4 produced prorennin levels ranging from 5 to 7%.

| Strain | Expression Plasmid | Percent of Total Cell Protein* | Culture O.D. 550 |
|---|---|---|---|
| HB101 | pPFZ-R2 | 13.1 | 0.5 |
|  | pPFZ-R4 | 7.1 | 0.5 |
| HB101 | pPFZ-R2 | 11.6 | 0.1 |
|  |  | 10.2 | 0.6 |
| HB101 | pPFZ-R2 | 15.4 | 0.3 |
|  |  | 11.7 | 0.5 |
|  | pPFZ-R4 | 7.0 | 1.0 |

*Based on densitometer scans of SDS-polyacrylamide gels.

The only difference between the two prorennin expression constructions (pPFZ-R2, and pPFZ-R4) in terms of nucleotide composition occurs in the sequences around the ribosome binding site and initiator codon of the prorennin gene. Yet there is significant variation in the levels of prorennin expression between cultures containing the different plasmids. The observed differences in prorennin expression can be attributed to the differences in the primary DNA sequence around the ribosome binding site. As first noted by Shine and Dalgarno (1974, Proc. Natl. Acad. Sci PNAS 71:1342–1342), there is a purine-rich sequence centered about 10 nucleotides upstream from the initiator codon that is complementary to the 3'-terminal sequence of 16S ribosomal RNA. An overwhelming body of evidence now supports the role of mRNA to rRNA base pairing in the selection of protein synthesis initiation sites by E. coli ribosomes. Ribosome binding sites from many bacterial and phage mRNAs have been sequenced and a consensus Shine-Dalgarno sequence has been determined to be: TAAG-GAGGT. Three parameters influence the efficiency of the Shine-Dalgarno interaction: 1) the length of complementarity; 2) the distance between the Shine-Dalgarno sequence and the initiator codon; and 3) the extent to which the Shine-Dalgarno sequence is masked by secondary structure.

Examination of the area around the S.D. sequence of each of the above two expression plasmids:

|  | DNA (Consensus) Sequence | spacing (bp) |
|---|---|---|
| S.D. | TAAGGAGGT |  |
| trpL | AAGTTCACGTAAAAAGGGTATCGACA ATG | 7 |
| pPFZ-R2 | AAGTTCACGTAAAAAGGAGAATTC ATG | 5 |
| pPFZ-R4 | AAGTTCACGTAAAAAGGGTATCGAGAATTC ATG | 11 | shows that the length of the complementarity in pPFZ-R2 is 6 contiguous nucleotides, whereas the other has only 3 contiguous nucleotides. Also, the spacing between the ribosome binding site and the initiator codon is 5 nucleotides in pPFZ-R2, which is very close to the spacing in the natural trpl gene initiator region where 7 nucleotides intervene; whereas, pPFZ-R4 has 11 nucleotides between the ribosome binding site and initiator codon. Another important feature of efficient ribosome binding sites recognized in pPFZ-R2 is a translational stop codon (TAA) in the same reading frame as the prorennin coding sequence just prior to the Shine-Dalgarno sequence. All these features of the pPFZ-R2 DNA sequence play a role in its highly efficient prorennin expression.

The degeneracy of the genetic code, of course, affords a certain degree of variation in composition of a given nucleotide sequence without altering the amino acid sequence of the protein encoded by said sequence. Thus, two or more different base sequences (synonymous codons) can be substituted in a given nucleotide sequence without changing the identity of the amino acids specified thereby. Further, it is possible to delete codons or to substitute one or more codons by codons other than degenerate codons to produce a structurally modified polypeptide but one which has substantially the same utility or activity of the polypeptide produced by the unmodified DNA molecule. Said two polypeptides are functionally equivalent, as are the two DNA molecules which give rise to their production, even though the differences between said DNA molecules are not related to degeneracy of the genetic code.

The codon for the 44 amino acid, threonine, is ACT instead of ACC. Due to the redundancy of the genetic code this does not change the amino acid at this position. Since this scheme employs the construction of a hybrid gene in which the section coding for the N-terminal portion of the hormone is made synthetically, the synthetic DNA allows for the design of a new coding sequence for that portion of prorennin. Because the amino acid sequence of prorennin is exactly maintained due to the redundancy of the genetic code, these kinds of sequence changes are insignificant and the gene produces an equivalent polypeptide to that produced in nature (with the exception of the N-terminal met).

The isolation of methionine prorennin expressed by bacterial (*E. coli*) transformants of this invention, its conversion to rennin and the milk-clotting activity of said rennin was demonstrated by the methodology described in British Patent Application 2,100,737A and by Emtage et al., Proc. Natl. Acad. Sci. 80:3671–3675 (1983).

Plasmids carrying an *E. coli* trp promoter-operator fragment, an ATG initiation codon, either the ribosome binding site comprising R2 or R4, and cDNA gene sequences encoding bovine growth hormone, porcine growth hormone or human epidermal growth factor have also been constructed, and when introduced into *E. coli*, resulted in highly efficient expression of the heterologous proteins. The nucleotide sequence of the vector, promoter, and ribosome binding site up to the ATG initiation codon were essentially the same as described above for the prorennin expression plasmids. The expression levels of the heterologous protein produced by these various constructs were determined by SDS-polyacrylamide gel electrophoresis followed by scanning densitometry. The relative levels of expression obtained with these cultures were similar to those observed with prorennin expression. That is, animal growth hormone expression plasmids containing the R2 version of the ribosome binding site exceeded the expression levels of the R4 version by approximately 4 to 5 fold; the ultimate expression level in *E. coli* cells was around 25% to 30% of the total cellular protein.

The scheme used to achieve expression of the bGH and pGH genes was essentially the same as the method published by P. Seeburg et al.(1983, DNA 2137–45) for the expression of animal growth hormones. It confirmed construction of a composite gene consisting of a cloned synthetic DNA and cloned cDNA sequences. This construction design allowed for the direct expression in *E. coli* of bGH and pGH without the signal sequence by introducing a translation initiation codon for the first amino acid of the mature hormone. The use of synthetic DNA also allowed for the design of a new coding sequence for the amino terminal region of the bGH and pGH genes. The amino acid sequences encoded by the synthetic regions of the growth hormone genes were exactly maintained due to the redundancy of the genetic code.

The plasmid containing the bGH cDNA was obtained as described by Miller et al., J. Biol. Chem. 255, 7521 (1980) and was designated pBGH-102. It is equivalent to plasmid BP348 of Miller et al. The nucleotide sequence of bGH mRNA and its corresponding amino acid sequence as predicted by the nucleotide sequence were previously published (Miller, W., et al., loc. cit.). The restriction fragment containing the tryptophan promoter-operator and ribosome binding site sequences were obtained from ptrpL1-R2 and -R4. The sequences of the synthetic double-stranded DNA used to modify the amino and carboxy termini of the growth hormone genes were extracted from the paper by Seeburg et al. (1983, DNA 2; 37–45). The oligonucleotides were synthesized, as noted above, using the phosphoramidite chemistry (Caruthers, et al.) and fragments were assembled from single-stranded oligomers, 11–16 bases long. The N-terminal synthetic DNA encodes the artificial ATG initiation codon for protein synthesis and the first 23 amino acid codons of bGH. To facilitate its insertion into pBR322 DNA, this synthetic fragment also included 4-base single-strand cohesive ends on the 5' ends corresponding in sequence to the cohesive ends generated by restriction endonucleases EcoRI and HindIII. The desired ligation product was isolated from a 5% polyacrylamide gel as a band of approximately 80 bp. The purified DNA was then ligated with pBR322 DNA which had been previously digested with restriction endonucleases EcoRI and HindIII, and transformed into competent *E. coli* cells. The cloned synthetic DNA was subject to DNA sequence analysis using the chemical degradation method (Maxam and Gilbert, 1980, Methods Enzymol 65; 499) to ensure the integrity of the modified bGH sequence.

Figure 5A:
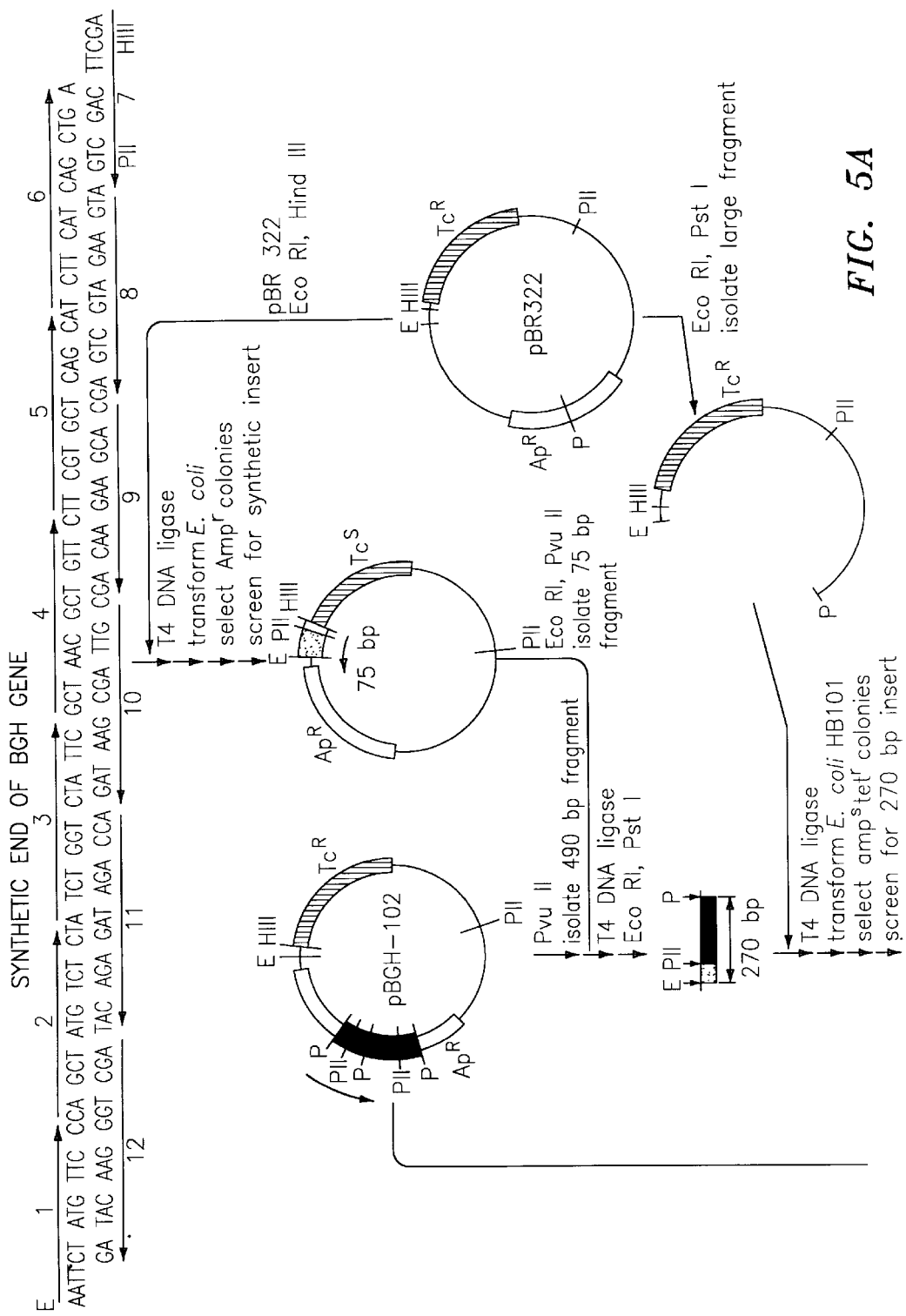
FIG. 5. Scheme for construction of plasmids containing the full length bGH gene and expression sequences. Plasmid pBGH-102 contains the bGH cDNA sequences (dark box) cloned into the ampicillin resistance gene in pBR322. The synthetic DNA coding for a new amino terminus of bGH was inserted into the EcoRI and HindIII sites of pBR322 (dotted box). Various in vitro manipulations were performed to construct a plasmid, pBGH-212, that carries the complete modified bGH gene. Plasmid pBGH-212 was cleaved with EcoRI and DNA fragments containing different variations of the trp promoter-operator sequence were inserted. Arrows show 5'→3' direction of coding sequence, or direction of transcription.
Figure 5B:
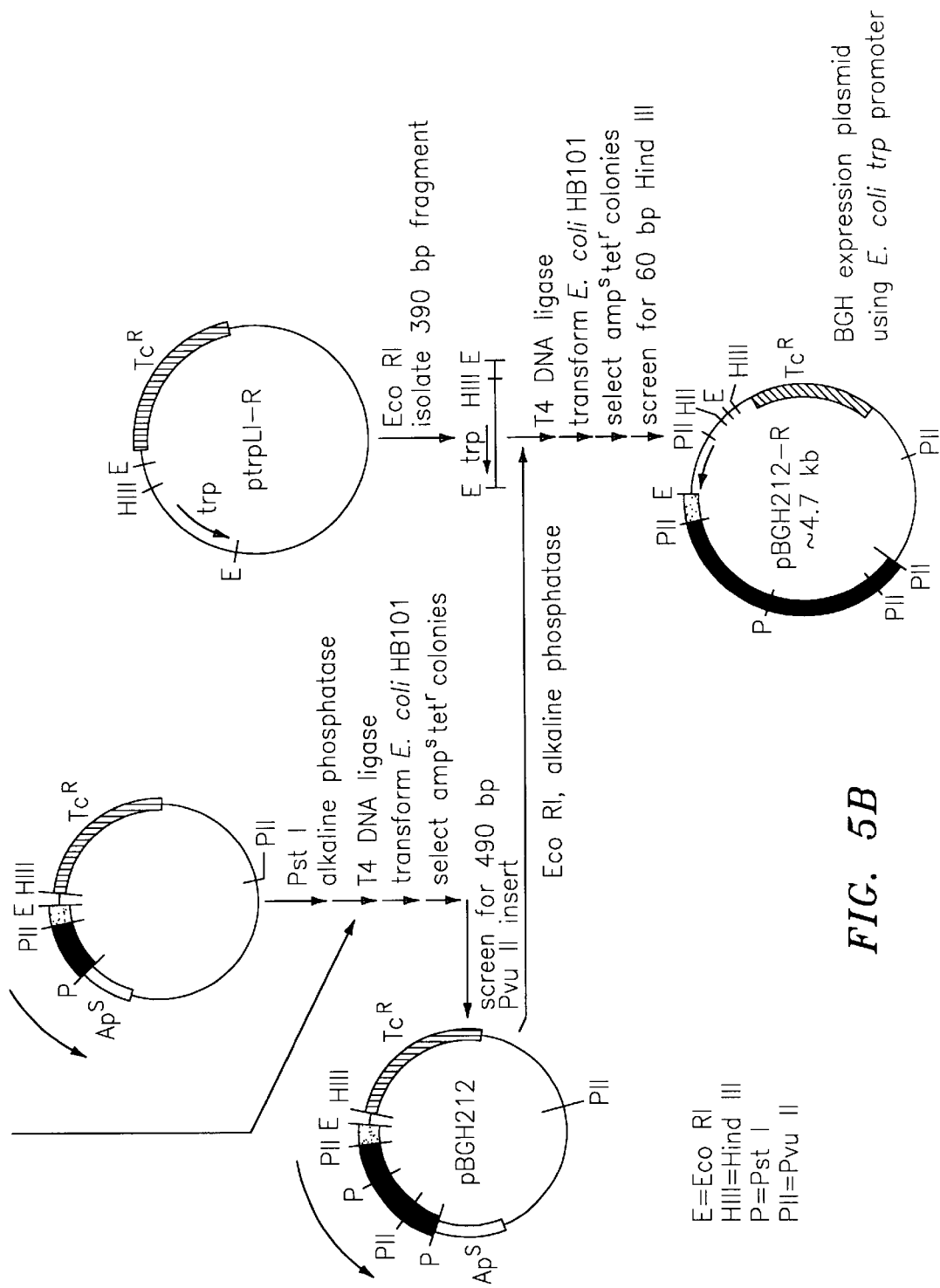
Figure 6A:
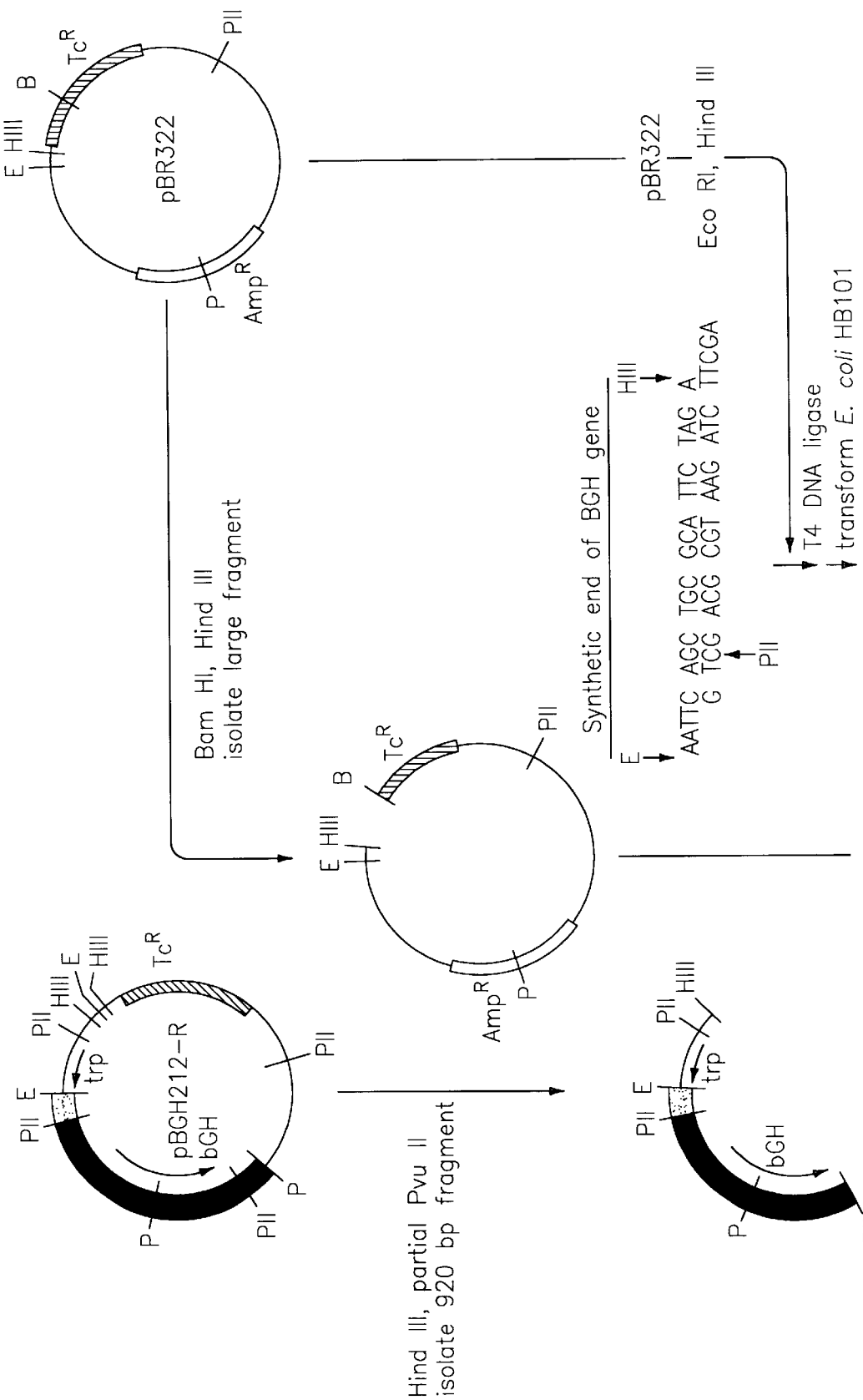
FIG. 6. Construction of a bacterial expression plasmid for bGH production. Plasmids pBGH-212-R carry a gene for the direct expression of mature bGH complete with trp promoter sequence (see FIG. 5). These plasmids were cleaved with HindIII, followed by partial digestion with PvuII, and two approximately 920 bp HindIII-PvuII fragments isolated. A synthetic DNA fragment coding for the C-terminus of bGH was inserted into the EcoRI and HindIII sites of pBR322 (white box). This subclone was cleaved with PvuII and BamHI, and the 365 bp DNA fragment was isolated. The large vector fragment (3995 bp) was isolated from pBR322 after cleavage with HindIII and BamHI. The two promoter-bGH gene containing fragments (920 bp) were separately mixed with the synthetic DNA containing fragment (365 bp) and the vector fragment (3995 bp). The mixtures were ligated with T4 ligase and used for transformation of competent E. coli HB101. The different bGH expression plasmids are referred to as pBGH-301, and pBGH-375. The arrows indicate the direction of transcription from the trp promoter sequence and the 5'→3' direction in the coding sequence.
Figure 6B:
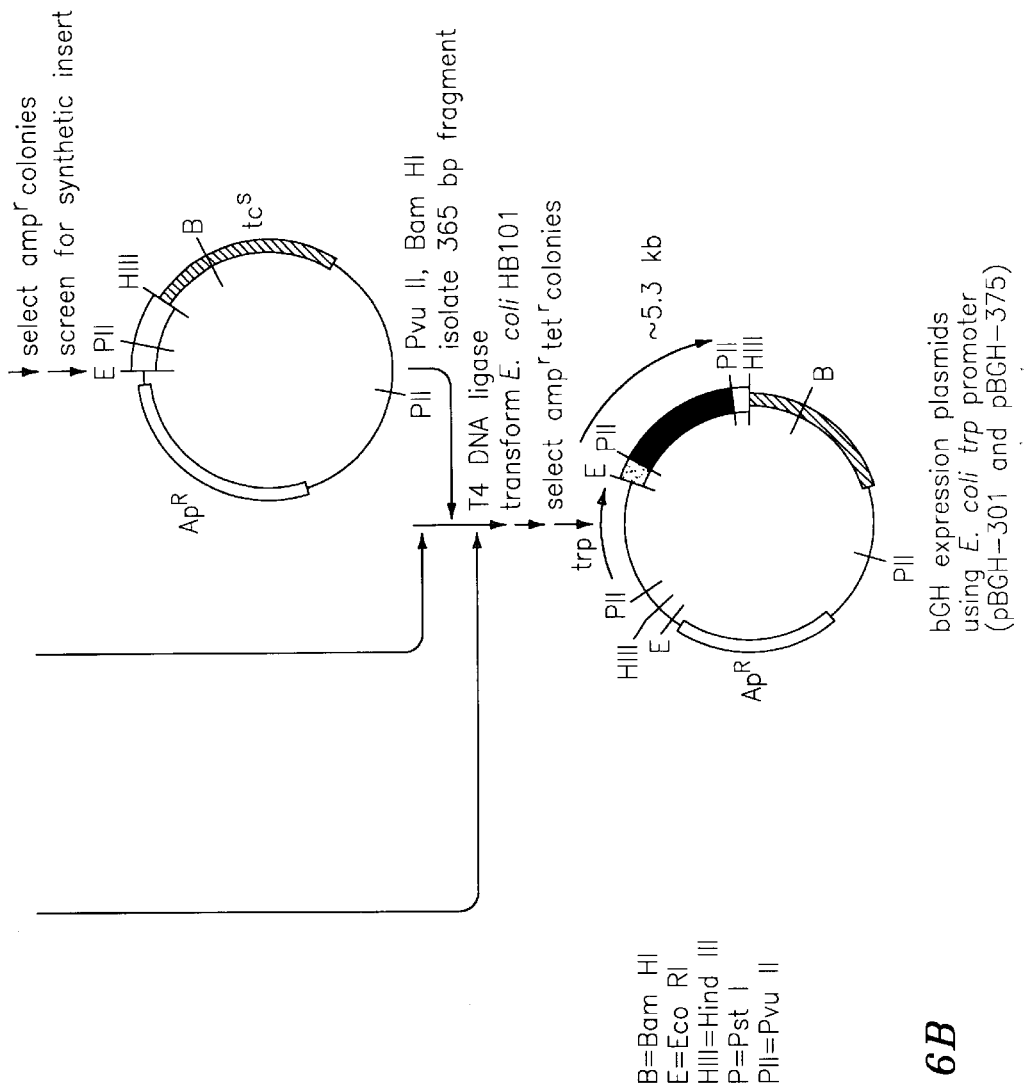

Expression vectors similar to the plasmids described by Seeburg et al. were constructed for both bGH and pGH in order to compare the effect of the altered ribosome binding site on the expression of mammalian genes other than prorennin. The experimental steps used for constructing the bGH expression plasmids are illustrated in FIGS. 5 and 6.

First the region from the cDNA clone, pBGH-102, encoding sequences for amino acids 23 to 86, was isolated on a 5% polyacrylamide gel and ligated to the cloned synthetic 75 bp EcoRI-PvuII fragment isolated from the pBR322 subclone which encodes sequences for the ATG initiation codon and the first 22 amino acids of bGH. The ligation mix was cleaved with restriction endonucleases EcoRI and PstI, and a 270 bp fragment was isolated from a 5% polyacrylamide gel and inserted into appropriately cleaved pBR322 DNA. Using these two sites, the EcoRI-PstI DNA fragment of modified bGH gene sequence can be inserted into the pBR322 plasmid so that only one orientation of insertion is possible. Plasmid DNA isolated from transformants obtained in the ligation were cleaved with EcoRI and PstI to verify the insertion of the 270 bp bGH gene fragment into the vector. Next, the 440 bp PstI DNA fragment from pBGH-102 containing the coding sequences of bGH amino acids 91 to 191 (plus the 3' untranslated region of the bGH cDNA) was inserted into the PstI site of this plasmid DNA in order to complete the reconstruction of the full length bGH gene. This PstI fragment could be inserted in two possible orientations relative to the rest of the bGH gene. According to the restriction map, the desired orientation of the insert would generate an approximately 490 bp PvuII fragment (completely internal to the bGH gene) while the wrong orientation would result in a 350 bp PvuII DNA fragment. Multiple isolates of both orientations were identified after cleavage of plasmid DNA from tetracycline-resistant transformants with restriction endonuclease PvuII. One of the plasmids identified in this manner was designated pBGH-212, and this full length bGH gene was further analyzed by restriction mapping and DNA sequencing to ensure the correctness of the plasmid construction.

The next step in the assembly of the bGH expression plasmids involved the insertion of EcoRI DNA fragments containing the *E. coli* trp promoter and ribosome binding sequences. The full length bGH clone, pBGH-212, was cleaved with restriction endonuclease EcoRI, treated with bacterial alkaline phosphatase, and ligated with two different approximately 390 bp EcoRI fragments containing the sequences required for bacterial expression of bGH. Two different ligations were done to insert the trp promoter-rbs fragments, each with slightly different nucleotide sequences in the gene initiation region, into pBGH-212. Competent cells of strain HB101 were transformed with each ligation reaction mix. Several tetracycline-resistant colonies from each transformation were picked and isolated plasmid DNA was subject to restriction endonuclease digestion analysis. The trp promoter-rbs containing fragment could insert into the pBGH-212 DNA in two possible orientations relative to the direction of transcription from the promoter. The orientation of the promoter-rbs insert which would result in transcription of the bGH gene generates a 60 bp HindIII DNA fragment, while the undesired orientation generates a 400 bp fragment. Multiple recombinant microorganisms from each ligation mix were identified with plasmids bearing the complete bGH gene adjacent to the trp promoter-rbs sequence in the configuration required for direct expression.

The construction of expression plasmids was initiated by isolating an approximately 920 bp HindIII-PvuII(partial) DNA fragment from the plasmids pBGH-212-R2 and pBGH-212-R4. This DNA fragment contains the trp promoter-rbs sequence and almost the entire bGH coding sequence (all but the last 4 amino acid residues and the stop codon). To express the entire hormone, a fragment of synthetic DNA encoding the C-terminal end of bGH was cloned into pBR-322. This 20 bp DNA fragment was synthesized as two separate oligomers, annealed to form a double-stranded fragment, and inserted into pBR322 DNA digested with restriction endonucleases EcoRI and HindIII. After digestion of plasmid DNA from this subclone with restriction endonucleases PvuII and BamHI, a 365 bp PvuII-BamHI DNA fragment was gel isolated and purified by electro-elution. The final expression plasmids were assembled by ligating the cloned synthetic C-terminal containing fragment (365 bp) with each of the trp promoter-rbs-bGH DNA fragment (920 bp) and the pBR322-derived vector fragment (3995 bp), as shown in FIG. 6. The full length bGH expression plasmids were identified by restriction endonuclease cleavage with PvuII. These bGH expression plasmids were further characterized by more precise determination of the restriction enzyme cleavage map. Additional characterization of these expression plasmids by DNA sequencing verified the modified bGH gene sequence and established the separate identity of the two different vectors; designated pBGH-301 and pBGH-375.

Translation of the DNA sequences of these expression plasmids predicts a hormone polypeptide of 191 amino acid residues. The estimated molecular weight of such a protein would be about 22,000. When cells containing the bGH expression plasmids pBGH-301 and pBGH-375 were grown under conditions known to induce trp promoter directed expression, the cells produced a comigrating protein the size of purified bGH protein (obtained from Miles) when total protein extracts were examined on SDS-polyacrylamide gel (Laemmli, U. 1970, Nature 277, 680). This band was not visible in protein extracts from cells containing the vector plasmid pBR322 grown under identical conditions. The bGH levels were estimated by densitometer gel scanning at 579 nm. The cultures containing the expression plasmid with the R2 version of the rbs (pBGH-301) produced bGH at levels of about 20% to 25% of the total cellular protein. Whereas, the cells containing the pBGH-375 expression plasmid with the R4 version of the rbs produced bGH at levels about 5% to 7% of the total cellular protein.

Figure 7A:
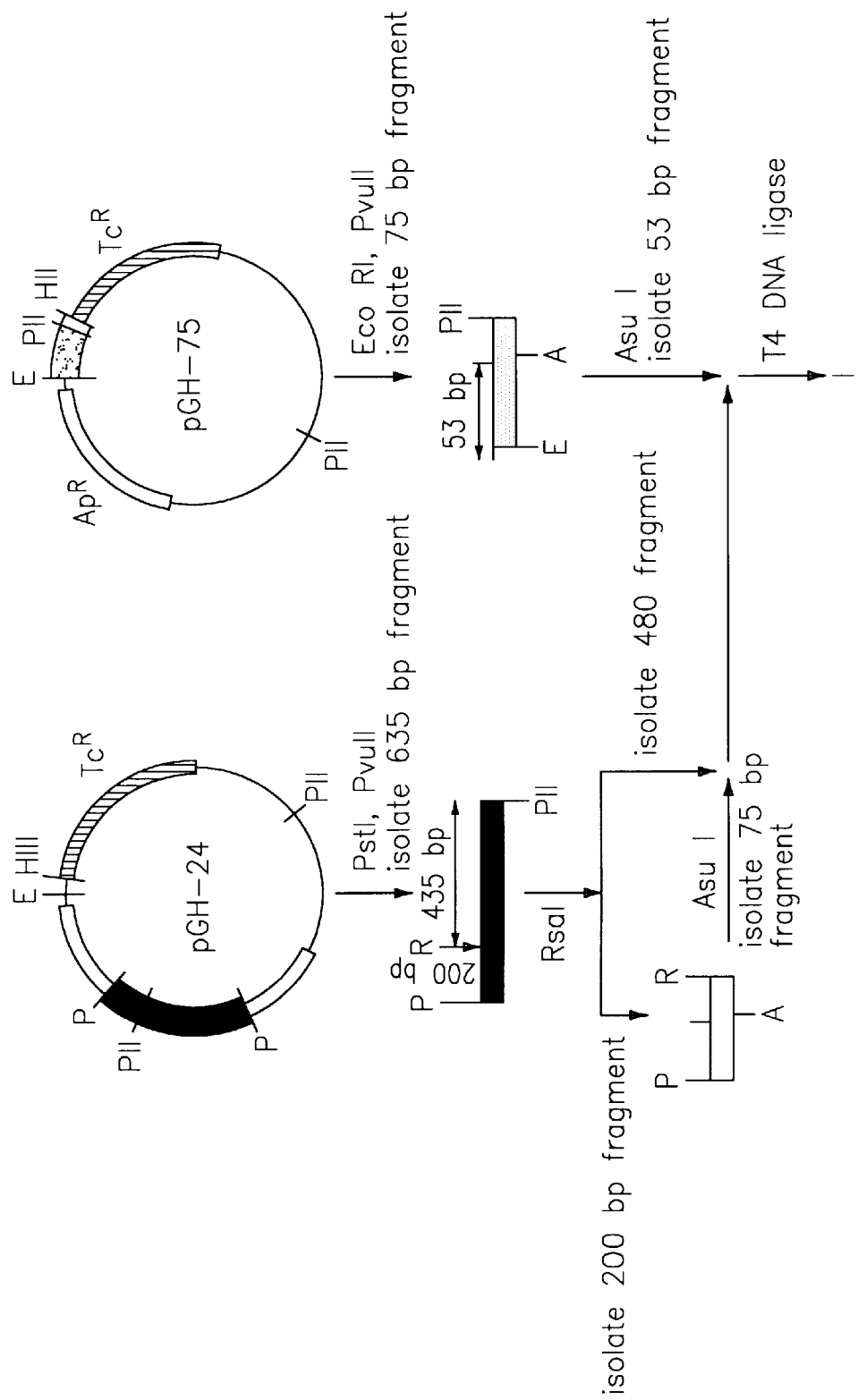
FIG. 7. Construction scheme for plasmids containing the full length pGH gene and expression sequences. Plasmid pGH-24 contains the pGH cDNA sequences (dark box) cloned into the ampicillin resistance gene in pBR322. The synthetic DNA coding for a new amino terminus of pGH was inserted into the EcoRI and HindIII sites of pBR322 (dotted box). Various in vitro manipulations were performed to construct a plasmid that carries the complete modified pGH gene. This plasmid was cleaved with EcoRI and DNA fragments containing different variations of the trp promoter-operator sequence were inserted. Arrows show 5' to 3' direction of coding sequence, or direction of transcription.
Figure 7B:
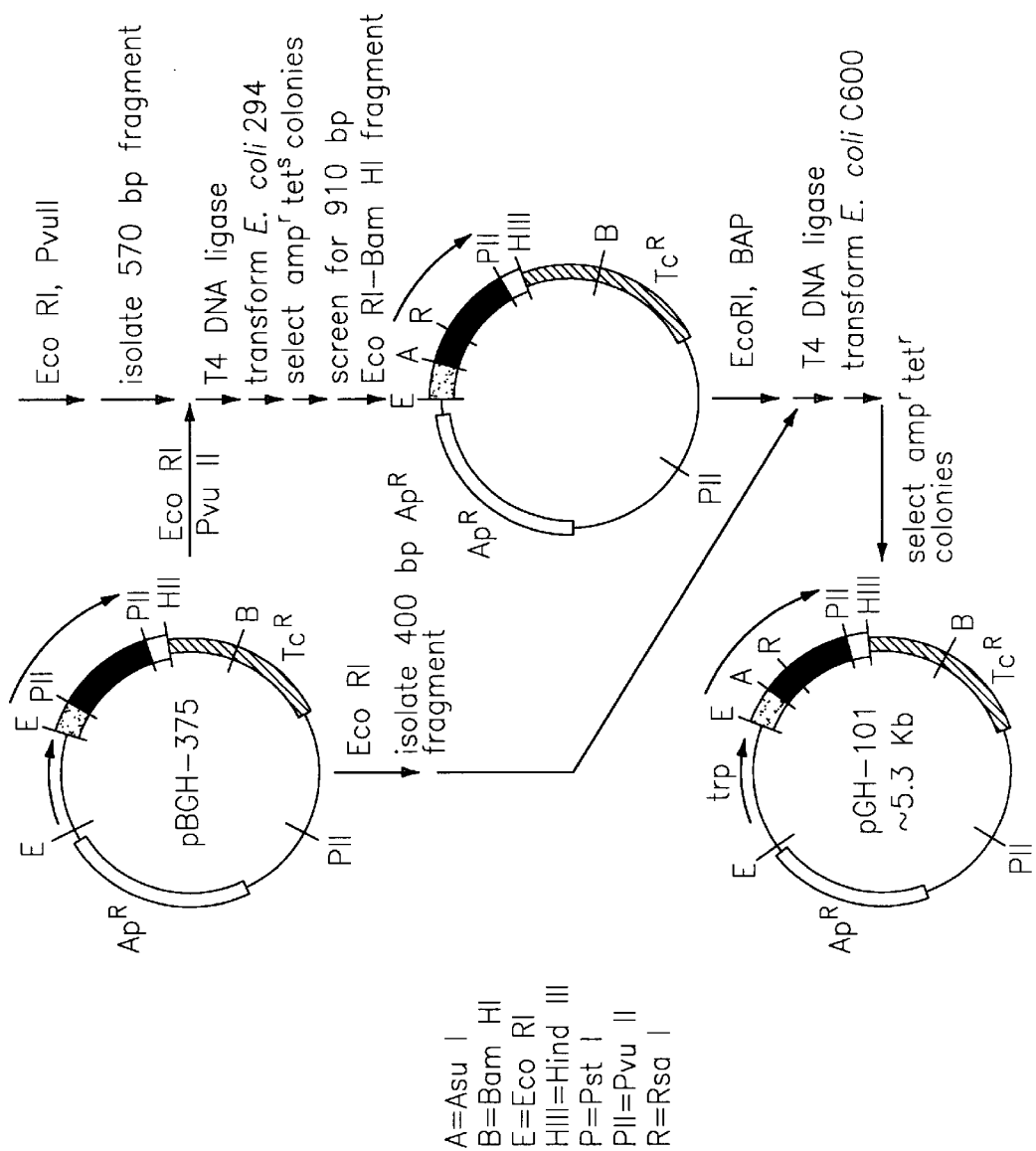

In the case of pGH expression, a scheme analogous to that used for bGH expression was employed. The sequence of the double-stranded DNA used to modify the amino terminal end of the pGH gene was essentially as described by Seeburg et al., (loc. cit.). The experimental steps used for constructing the pGH expression plasmids are illustrated in FIG. 7. First, the region from the cDNA clone (pGH 24) was substituted with the synthetic region of the pGH gene. Because the region coding for amino acid residues 22 and 23 of pGH lacked a PvuII site, the synthetic 5' part of the pGH hybrid gene was joined to the coding sequences derived from the cloned cDNA at an AsuI site which occurs at amino acid codons 16 and 17 in pGH-24. An AsuI site was also incorporated at the same position in the synthetic DNA coding for the amino terminal end of pGH. Due to the presence of additional AsuI sites in the cloned cDNA, the pGH gene was reconstructed from three different DNA fragments.

The 635 bp PstI-PvuII fragment isolated from pGH-24 was digested with RsaI and the resulting 200 bp PstI-RsaI fragment was further cleaved with AsuI. The modified gene was constructed by ligating together the cloned synthetic EcoRI-AsuI 53 bp fragment, the 75 bp AsuI-RsaI fragment, and the 480 bp RsaI-PvuII fragment. The product of this ligation was digested with EcoRI and PvuII, and a DNA fragment corresponding to 570 bp in size was isolated from a 5% polyacrylamide gel. This fragment was ligated with the EcoRI-PvuII (partial) vector fragment from the bGH expression plasmid pBGH-375 and transformed into competent cells of E. coli strain MM294 (ATCC 33625) and selected on plates containing ampicillin. This pre-expression plasmid (identified by the presence of a 910 bp EcoRI-BamHI fragment) contains the full length pGH gene, since the pGH and bGH proteins have the same C-terminal amino acid sequence.

The next step in the construction of the pGH expression plasmids involved the insertion of the approximately 390 bp EcoRI DNA fragments containing the E. coli trp operon promoter sequence and modified ribosome binding sites. The full length pGH plasmid was cleaved with restriction endonuclease EcoRI and ligated with separate versions of the EcoRI fragments containing the sequence needed for bacterial expression of pGH. Two different ligation reactions were made using expression fragments with slightly different nucleotide sequences in the region around the ribosome binding site. Competent cells of strain C600 were transformed with each ligation reaction. Plasmid DNA was isolated from several drug resistant colonies from each transformation and was subjected to restriction endonuclease digestion analyses. The trp promoter containing fragment could insert into the pre-expression plasmid in two possible orientations relative to the direction of transcription from the trp promoter. The orientation of the promoter insert fragment which would result in the transcription of the pGH gene generates a 920 bp HindIII DNA fragment, while the undesired orientation generates a 600 bp DNA fragment. Multiple isolates from each ligation reaction were identified with plasmids bearing the complete pGH gene adjacent to the trp promoter and rbs sequence in the configuration required for direct expression. Further characterization of these expression constructions was achieved by physical mapping with additional restriction endonucleases. Additional characterization of these pGH expression plasmids by DNA sequencing has established their separate identity at the nucleotide level. The two pGH expression plasmids were designated pGH-101 and pGH-107.

Translation of the DNA sequence of these pGH expression plasmids predicts a hormone polypeptide of 191 amino acids. The estimated molecular weight of such a protein would be about 22,000. When recombinant microorganisms comprising plasmids pGH-101 or pGH-107 were grown under conditions known to induce trp promoter directed expression, the cells produced a protein with a size of about 22,000 daltons. This band was absent from protein extracts prepared from cells containing the vector plasmid pBR322 grown under identical conditions. The level of pGH production was determined using densitometer scans of individual lanes of SDS-polyacrylamide gels. Several E. coli proteins fall into the 22,000 dalton size range and constitute about 2% to 5% of the total cell protein in control cell extracts. Correcting for the contribution of these native proteins, the pGH bands visible in the expression culture protein extract represent about 5% and 15% of the total cell protein for pGH-101 and pGH-107, respectively. The quantitation of pGH levels in cultures grown in the presence of tryptophan (100 μg/ml) showed reduced levels of pGH expression. This fact would imply that production in E. coli of the pGH protein was indeed under control of the trp promoter-operator as designed. The difference in expression levels in the case of pGH was similar to that observed in prorennin and bGH expression using the same ribosome binding site sequence.

Another example of efficient expression of a heterologous gene using the "R2" trp promoter-rbs is the production of human urogastrone or epidermal growth factor (hEGF) from a synthetic DNA sequence. The plan devised to achieve efficient bacterial production of hEGF employed the chemical construction of a DNA fragment containing the coding sequence of mature hEGF. This approach allowed for the direct expression of the mature hormone by introducing an ATG initiation codon for protein synthesis in front of the codon coding for the first amino acid residue of the mature EGF polypeptide. The synthetic gene is composed of 15 oligonucleotides, 12 to 45 bases in length. Three separate ligations were performed and the intermediate ligation products were isolated on a polyacrylamide gel. The purified intermediate ligation products were then ligated in the final assembly of the hEGF gene. To facilitate its insertion into plasmid pBR322 DNA, the synthetic hEGF gene was designed to contain EcoRI and HindIII restriction endonuclease cohesive ends at its termini. The hEGF synthetic DNA was ligated with pBR322 DNA cleaved with EcoRI and HindIII and the synthetically derived region of the plasmid was analyzed by DNA sequencing (Maxam and Gilbert, loc. cit.) to ensure correctness.

Vectors for the expression of hEGF in E. coli were constructed using the trp promoter-rbs fragment previously used for high level expression of prorennin, bGH, and pGH. The construction of the EGF expression plasmids was initiated by cleavage of the pBR322-EGF subclone with the restriction endonuclease EcoRI and subsequent dephosphorylation with bacterial alkaline phosphatase. The expression plasmids were constructed using the EcoRI fragments containing the trp promoter-rbs sequence. Two different ligations were done employing the trp promoter-rbs fragments with slightly different nucleotide sequences in the region around the ribosome binding site. Competent cells of E. coli strain HB101 were transformed with each ligation reaction. Several drug resistant colonies from each transformation were picked and isolated plasmid DNA was subject to restriction endonuclease cleavage analysis. The trp promoter-rbs containing fragment could be inserted into the EGF subclone in two possible orientations relative to the direction of transcription from the promoter. The orientation of the promoter insert fragment which would result in expression of the synthetic EGF gene generates a 510 bp HindIII DNA fragment, whereas the undesired orientation generates a 200 bp HindIII DNA fragment. Multiple isolates from each ligation reaction were identified with plasmids bearing the EGF gene adjacent to the bacterial promoter-rbs sequence in the configuration required for direct expression. DNA sequence analysis of the expression plasmids confirmed that the EGF coding sequence directly follows the E. coli trp promoter-rbs as desired. The ATG initiation codon follows the ribosome binding site sequence by 5 and 11 nucleotides in the EGF expression plasmids designated pEGF-R2 and PEGF-R4, respectively.

Translation of the DNA sequence of the EGF expression plasmids predicts a 54 amino acid poly-peptide containing six cysteine residues, which are thought to form three intrachain disulphide bonds. The estimated molecular weight of such a hormone would be about 6,353. Cultures of a mutant strain of E. coli designated as lon (Gottesman et al., J. Bacteriol. 148, 265, 1981), available from the E. coli Genetic Stock Center, Yale University, New Haven, Conn., as strain No. ECGSC-6436, were transformed with EGF expression plasmids and grown under conditions known to induce trp promoter directed expression. This mutant strain, which lacks one of several proteases present in wild-type cells, was used to minimize proteolysis of the bacterially produced hEGF.

Total protein extracts of these expression cultures were examined on 15% SDS-polyacrylamide gels in an effort to determine the level of EGF production. Although there was relatively poor resolution of the low molecular weight polypeptides (including purified mouse-EGF obtained from a commercial source), there appeared to be more protein in the EGF molecular weight range in the extracts from expression cultures compared to control extracts. Densitometer scans of individual lanes of the SDS-polyacrylamide gel were run. Cellular proteins less than 10,000 daltons in size constitute about one percent of the total cellular protein in control extracts. Correcting for the contribution of these native proteins, the putative EGF levels in the expression culture protein extracts corresponds to about 3 to 5 percent of the total cellular protein.

I claim:

1. A process for using an E. coli comprising an expression plasmid comprising:

(i) an E. coli trp promoter;
   (ii) the nucleotide sequence TAAAAAGGAGAATTC encoding a ribosome binding site for translation of element (iii); and
   (iii) a structural gene coding the amino acid sequence of a heterologous protein, to produce said heterologous protein, which process comprises cultivating said E. coli comprising said expression plasmid in an aqueous medium comprising an assimilable source of carbon, nitrogen and inorganic salts.

2. The process according to claim 1 wherein said heterologous protein is bovine prorennin.

3. A process for using an E. coli according to claim 2 further comprising isolating the prorennin and converting the prorennin to rennin.

4. The process according to claim 1 wherein said heterologous protein is mammalian growth hormone.

5. A process for using an E. coli comprising an expression plasmid comprising:

(i) an E. coli trp promoter;
   (ii) the nucleotide sequence TAAAAAGGGTATCGAGAATTC encoding a ribosome binding site for translation of element (iii); and
   (iii) a structural gene coding the amino acid sequence of a heterologous protein, to produce said heterologous protein, which process comprises cultivating said E. coli comprising said expression plasmid in an aqueous medium comprising an assimilable source of carbon, nitrogen and inorganic salts.

6. The process according to claim 5 wherein said heterologous protein is bovine prorennin.

7. A process for using an E. coli according to claim 6 further comprising isolating the prorennin and converting the prorennin to rennin.

8. The process according to claim 5 wherein said heterologous protein is mammalian growth hormone.

9. A process for using a microorganism selected from the group consisting of E. coli K-12 strains comprising plasmid pPFZ-R2 and E. coli strains comprising plasmid pPFZ-R4 to produce prorennin, which process comprises cultivating said microorganism in an aqueous nutrient medium comprising an assimilable source of carbon, nitrogen and inorganic salts until a substantial amount of prorennin is expressed; and isolating said prorennin.

10. The process according to claim 9 wherein the microorganism is *E. coli* ATCC 39544 or *E. coli* ATCC 39543.

11. A process for using a microorganism according to claim 10 further comprising converting the prorennin to rennin.

12. A process for using a microorganism according to claim 9 further comprising converting the prorennin to rennin.

13. A process for producing heterologous protein in *E. coli* which comprises cultivating, in an aqueous medium comprising an assimilable source of carbon, nitrogen and inorganic salts, an *E. coli* comprising an expression plasmid comprising:

(i) an *E. coli* trp promoter;

(ii) the nucleotide sequence TAAAAAGGAGAATTC encoding a ribosome binding site for translation of element (iii); and (iii) a structural gene coding the amino acid sequence of said heterologous protein.

14. The process according to claim 13 wherein said heterologous protein is bovine prorennin.

15. A process for producing rennin which comprises the process according to claim 14, isolating the prorennin and converting the prorennin to rennin.

16. The process according to claim 13 wherein said heterologous protein is mammalian growth hormone.

17. A process for producing heterologous protein in *E. coli* which comprises cultivating, in an aqueous medium comprising an assimilable source of carbon, nitrogen and inorganic salts, and *E. coli* comprising an expression plasmid comprising:

(i) an *E. coli* trp promoter;

(ii) the nucleotide sequence TAAAAAGGGTATCGAGAATTC encoding a ribosome binding site for translation of element (iii); and (iii) a structural gene coding the amino acid sequence of said heterologous protein.

18. The process according to claim 17 wherein said heterologous protein is bovine prorennin.

19. A process for producing rennin which comprises the process according to claim 18, isolating the prorennin and converting the prorennin to rennin.

20. The process according to claim 17 wherein said heterologous protein is mammalian growth hormone.

21. A process for producing prorennin which comprises cultivating, in an aqueous nutrient medium comprising an assimilable source of carbon, nitrogen and inorganic salts, a microorganism selected from the group consisting of *E. coli* K-12 strains comprising plasmid pPFZ-R2 and *E. coli* K-12 strains comprising plasmid pPFZ-R4 until substantial amounts of prorennin are expressed and isolating said prorennin.

22. The process according to claim 21 wherein the microorganism is *E. coli* ATCC 39544 or *E. coli* ATCC 39543.

23. A process for producing rennin which comprises the process according to claim 22 and converting the prorennin to rennin.

24. A process for producing rennin which comprises the process according to claim 21 and converting the prorennin to rennin.

* * * * *